(12) United States Patent
Dharmakumar et al.

(10) Patent No.: US 12,279,855 B2
(45) Date of Patent: Apr. 22, 2025

(54) HIGHLY-TIMED RESOLVED MYOCARDIAL BLOOD-OXYGEN-LEVEL-DEPENDENT MAGNETIC RESONANCE IMAGING

(71) Applicant: Cedars-Sinai Medical Center, Los Angeles, CA (US)

(72) Inventors: Rohan Dharmakumar, Moorpark, CA (US); Hsin-Jung Yang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1046 days.

(21) Appl. No.: 17/043,453

(22) PCT Filed: Apr. 26, 2019

(86) PCT No.: PCT/US2019/029316
§ 371 (c)(1),
(2) Date: Sep. 29, 2020

(87) PCT Pub. No.: WO2019/210145
PCT Pub. Date: Oct. 31, 2019

(65) Prior Publication Data
US 2021/0022640 A1    Jan. 28, 2021

Related U.S. Application Data

(60) Provisional application No. 62/662,869, filed on Apr. 26, 2018.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0044* (2013.01); *A61B 5/0263* (2013.01);
(Continued)

(58) Field of Classification Search
CPC ..... A61B 5/055; A61B 5/0044; A61B 5/0263; A61B 5/14542; G01R 33/50; G01R 33/56509
See application file for complete search history.

(56) References Cited

U.S. PATENT DOCUMENTS 11,445,912 B2    9/2022    Dharmakumar et al.
11,566,543 B2    1/2023    Janicki
(Continued)

FOREIGN PATENT DOCUMENTS

CA    3092698 A1    10/2019
EP    2916133 A1    9/2015
(Continued)

OTHER PUBLICATIONS

Vohringer, M., et al., "Oxygenation-sensitive CMR for assessing vasodilator-induced changes of myocardial oxygenation," Journal of Cardiovascular Magnetic Resonance. vol. 12(20), 2010. p. 1-7 (Year: 2010).*
(Continued)

*Primary Examiner* — Sean A Frith
(74) *Attorney, Agent, or Firm* — Suwei Zhu; Linda B. Huber; Nixon Peabody LLP

(57) ABSTRACT

The invention provides various methods for imaging a subject's cardiovascular system. The imaging methods may be used to diagnose or prognose various cardiovascular diseases in the subject, without contrast agents or radioactive tracers.

20 Claims, 2 Drawing Sheets

(51) Int. Cl.
A61B 5/026 (2006.01)
A61B 5/145 (2006.01)
G01R 33/50 (2006.01)
G01R 33/565 (2006.01)

(52) U.S. Cl.
CPC .......... A61B 5/14542 (2013.01); G01R 33/50 (2013.01); G01R 33/56509 (2013.01)

(56) References Cited

U.S. PATENT DOCUMENTS

| | | |
|---|---|---|
| 2003/0017612 A1 | 1/2003 | Gerber |
| 2003/0065258 A1 | 4/2003 | Gupta et al. |
| 2005/0238727 A1 | 10/2005 | Cagnoni |
| 2006/0210478 A1 | 9/2006 | Weisskoff |
| 2006/0239920 A1 | 10/2006 | Kucharczyk et al. |
| 2007/0259966 A1 | 11/2007 | Cagnoni |
| 2007/0299136 A1 | 12/2007 | Johnson |
| 2008/0267861 A1 | 10/2008 | Lieu et al. |
| 2009/0161938 A1 | 6/2009 | Shekar et al. |
| 2009/0259121 A1 | 10/2009 | Simonetti et al. |
| 2009/0299436 A1 | 12/2009 | Mushahwar et al. |
| 2010/0232671 A1 | 9/2010 | Dam et al. |
| 2011/0076255 A1 | 3/2011 | Pecora et al. |
| 2012/0189538 A1 | 7/2012 | Gordi et al. |
| 2013/0289397 A1 | 10/2013 | Bienenstock |
| 2014/0053837 A1 | 2/2014 | Klein et al. |
| 2014/0088406 A1 | 3/2014 | Dharmakumar et al. |
| 2014/0121511 A1 | 5/2014 | Kadrmas et al. |
| 2014/0170069 A1 | 6/2014 | Dharmakumar et al. |
| 2014/0257083 A1 | 9/2014 | McVeigh et al. |
| 2015/0196207 A1 | 7/2015 | Friedrich et al. |
| 2015/0230762 A1 | 8/2015 | Alpert et al. |
| 2015/0231357 A1* | 8/2015 | Lu .......................... A61M 16/20 600/301 |
| 2016/0045841 A1 | 2/2016 | Kaplan |
| 2016/0104279 A1 | 4/2016 | Li et al. |
| 2016/0139225 A1* | 5/2016 | Basha ................ G01R 33/4835 324/309 |
| 2016/0220115 A1 | 8/2016 | Fisher et al. |
| 2017/0128025 A1 | 5/2017 | Chen |
| 2017/0340266 A1 | 11/2017 | Gardner et al. |
| 2018/0185519 A1 | 7/2018 | Dharmakumar et al. |
| 2018/0217217 A1* | 8/2018 | Weingartner .......... G01R 33/50 |
| 2018/0271375 A1 | 9/2018 | Dharmakumar et al. |
| 2019/0038781 A1 | 2/2019 | Dharmakumar et al. |
| 2019/0302211 A1* | 10/2019 | Cai ........................... G06T 7/20 |
| 2022/0054661 A1 | 2/2022 | Dharmakumar et al. |
| 2022/0117508 A1 | 4/2022 | Dharmakumar et al. |

FOREIGN PATENT DOCUMENTS

| | | | |
|---|---|---|---|
| EP | 3784118 A1 | 3/2021 | |
| JP | 2011083592 A | 4/2011 | |
| JP | 2021521966 A | 8/2021 | |
| WO | 2012/151583 A1 | 11/2012 | |
| WO | 2013041834 A1 | 3/2013 | |
| WO | 2015/123598 A1 | 8/2015 | |
| WO | WO-2017059302 A1 * | 4/2017 | ........... A61B 5/0044 |
| WO | 2019/210145 A1 | 10/2019 | |
| WO | 2020/163783 A1 | 8/2020 | |

OTHER PUBLICATIONS

International Search Report and Written Opinion for PCT/US2016/54890 dated Feb. 3, 2017, 23 pages.
International Preliminary Report on Patentability for PCT/US2016/054890 dated Apr. 12, 2018, 12 pages.
International Search Report and Written Opinion for PCT/US2019/29316 dated Jul. 15, 2019, 11 pages.
International Search Report and Written Opinion for PCT/US2020/17320, dated Jun. 10, 2020, 10 pages.
Al Jaroudi et al., Regadenoson: A New Myocardial Stress Agent, J. Am. Coll. Cardiol., 2009, 54(13), pp. 1123-1130.
Arnold et al., Myocardial Oxygenation in Coronary Artery Disease: In sights From Blood Oxygen Level-Dependent Magnetic Resonance Imaging at 3 Tesla, Journal of the American College of Cardiology, 2012, 59:22, pp. 1954-1964.
Avants et al., A reproducible evaluation of ANTs similarity metric performance in brain image registration, Neuroimage, 2011, 54, pp. 2033-2044.
Chaddad, Automated Feature Extraction in Brain Tumor by Magnetic Resonance Imaging Using Gaussian Mixture Models, International Journal of Biomedical Imaging, 2015, retrieved from: "https://www.ncbi.nlm.nih.gov/pmc/articles/PMC4469084/pdf/IJBI2015-868031.pdf" on Jan. 10, 2017, 11 pages.
Doneva et al., Compressed Senseing Reconstruction for Magnetic Resonance Parameter Mapping, Magnetic Resonance in Medicine, 2010, vol. 64, pp. 1114-1120.
Felmlee et al., Mechanism-Based Pharmacodynamic Modeling, Methods Mol Biol. 2012, 929, pp. 583-600.
Gabizon et al., Liposomes as in Vivo Carriers of Adriamycin: Reduced Cardiac Uptake and Preserved Antitumor Activity in Mice, Cancer Research, 1982, 42, pp. 4734-4739.
Giri et al., T2 quantification for improved detection of myocarial edema, Journal of Cardiovascular Magnetic Resonance, 2009, 11:56, pp. 1-13.
Gordi et al., A population pharmacokinetic/pharmacodynamic analysis of regadenoson, an adenosine A2A-receptor agonist, in healthy male volunteers, Clinical pharmacokinetics, 2006, 45, pp. 1201-1212.
Jaroudi et al., Expression profiling of DNA repair genes in human ooxytes and blastocysts using microarrays, Human Reproduction, 2009, 24(10), pp. 2649-2655.
Karamitsos et al., Relationship Between Regional Myocardial Oxygenation and Perfusion in Patients With Coronary Artery Disease: Insights From Cardiovascular Magnetic Resonance and Positron Emission Tomography, Circ. Cardiovasc. Imaging, 2010, 3:1, pp. 32-40.
Kober et al., Myocardial arterial spin labeling, Journal of Cardiovascular Magnetic Resonance, 2016, 18:22, pp. 11-16.
Pang et al., Accelerated Whole-Heart Coronary MRA Using Motion-Corrected Sensitivity Encoding with Three-Dimensional Projection Reconstruction, Magnetic Resonance in Medicine, 2015, vol. 73, pp. 284-291.
Parnham et al., Impaired Myocardial Oxygenation Response to Stress in Patients With Chronic Kidney Disease, J. Am. Heart. Assoc. 2015, 4(8), e002249, 12 pages.
Prieto, C., Undersampled Reconstruction Techniques to Speec up MRI, UCL PET-MRI Methodology Symposium, 2016, Division of Imaging Sciences and Biomedical Engineering King's College London, pp. 1-41.
Seemann, Improvements to Quantification Algorithms for Myocardial Infarction in CMR Images, 2013, retrieved from: "http://lup.lub.lu.se/luur/download?func=downloadFile&recordOld=4128314&fileOld=4128321" on Jan. 10, 2017, 55 pages.
Tsaftaris et al., Ischemic Extent as a Biomarker for Characterizing Severity of Coronary Artery Stenosis With Blood Oxygen-Sensitive MRI, J. Magn. Reson. Imaging, 2012, 35, pp. 1338-1348.
Vohringer et al., Oxygenation-sensitive CMR for assessing vasodilator-induced changes of myocardial oxygenation, Journal of Cardiovascular Magnetic Resonance, 2010, retrieved from: "https://www.ncbi.nlm.nih.gov/pmc/articles/PMC2861023/pdf/1532-429X-12-20.pdf" on Jan. 10, 2017, 7 pages.
Wang et al. Color image segmentation using pixel wise support vector machine classification, Pattern Recognition, 2011, 44(4), pp. 777-787.
Wright et al., Non-Cartesian Parallel Imaging Reconstruction, Journal of Magnetic Resonance Imagine, 2014, vol. 40, pp. 1022-1040.
Yang et al., Assessment of Myocardial Reactivity to Controlled Hypercapnia with Free-Breathing T2-Prepared Cardiac Blood Oxygen Level-Dependent MR Imaging, Radiology, 2014, vol. 272(2), pp. 397-406.
Yang et al., Free-Breathing, Motion-Corrected, Highly Efficient Whole Heart T2 Mapping at 3T with Hybrid Radial-Cartesian Trajectory, Magnetic Resonance in Medicine, 2016, vol. 75, pp. 126-136.

(56) References Cited

OTHER PUBLICATIONS

Yang et al., Towards reliable myocardial blood-oxygen-level-dependent (Bold) CMR using late effects of regadenoson with simultaneous 13n-ammonia pet validation in a whole-body hybrid PET/MR system, Journal of Cardiovascular Magnetic Resonance, 2016, 18 (Suppl 1): O19, 3 pages.

Yang et al., Arterial CO2 as a Potent Coronary Vasodilator: A Preclinical PET/MR Validation Study with Implication for Cardiac Stress Testing, J Nucl Med, 2017, vol. 58, pp. 953-960.

Yang et al., Beat-by-Beat Dynamic Assessment of Myocardial Oxygenation with Highly Time-Resolved, Free-breathing, Ungated Cardiac T2 Bold MRI Using a Low-Rank Tensor Formulation, Joint Annual Meeting ISMRM-ESMRMB, 2018, Abstract Only.

Yang et al., Accurate Needle-Free Assessment of Myocardial Oxygenation for Ischemic Heart Disease in Canines Using Magnetic Resonance Imaging, Sci Transl. Med, 2019, vol. 11, pp. 1-10.

Zoghbi et al., Selective adenosine agonists and myocardial perfusion imaging. J.Nucl. Cardiol., 2012, 19(1), pp. 126-141.

Miller, D, Impact of Selective Adenosine A2A Receptor Agonists on Cardiac Imaging, Journal of American College of Cardiology, 2005, vol. 46(11), pp. 2076-2078.

Hsin-Jung Yang, Oral presentation at 19th Annual Scientific Sessions of Society for Cardiovascular Magnetic Resonance (SCMR), "Towards Reliable Myocardial Blood-Oxygen-Level-Dependent (BOLD) CMR Using Late Effects of Regadenoson with Simultaneous 13N-ammonia PET Validation in a Whole-body Hybrid PET/MR System", Jan. 29, 2016.

Proceedings from the 20th annual SCMR Scientific Sessions, Feb. 1-4, 2017, Abstract Supplement.

Carneiro et al., MRI Relaxometry: Methods and Applications, Brazillian Journal of Physics, 2006, vol. 36(1A), pp. 9-15.

Gao et al., Highly Automatic Quantification of Myocardial Oedema in Patients with Acute Myocardial Infarction using Bright Blood T2-Weighted CMR, Journal of Cardiovascular Magnetic Resonance, 2013, vol. 15(28), pp. 1-12.

Li et al., Myocardial Signal Respone to Dipyridamole and Dobutamine: Demonstration of the Bold Effect Using a Double-Echo Gradient-Echo Sequence, Magnetic Resonance in Medicine, 1996, vol. 36(1), pp. 16-20.

Stalder et al., Robust Cardiac BOLD MRI Using an fMRI-Like Approach with Repeated Stress Paradigms, Magnetic Resonance in Medicine, 2015, vol. 73, pp. 577-585.

Supplementary European Search Report for EP 19792195 dated Dec. 8, 2021, 8 pages.

International Preliminary Report on Patentability for PCT/US2019/29316 dated Oct. 27, 2020, 8 pages.

Supplementary European Search Report for EP 20752805 dated Jan. 16, 2023, 14 pages.

Salerno et al., Adenosine Stress Cardiovascular Magnetic Resonance With Variable-Density Spiral Pulse Sequences Accurately Detects Coronay Artery Disease Initial Clinical Evaluation, Circulation Cardiovascular Imaging, 2014, vol. 7 (4), pp. 639-646.

Pelletier-Galarneau et al., Effects of Hypercapnia on Myocardial Blood Flow in Healthy Human Subjects, The Journal of Nuclear Medicine, 2018, vol. 59(1), pp. 100-106.

Santarelli et al., New Imaging Frontiers in Cardiology: Fast and Quantitative Maps from Raw Data, Current Pharmaceutical Design, 2017, vol. 23, pp. 3268-3284.

Doneva et al., Compressed Sensing Reconstruction for Magnetic Resonance Parameter Mapping, Magnetic Resonance in Medicine, 2010, vol. 64, pp. 1114-1120.

Yang, Technological Advances and New Physiological Insights for Reliably Probing Myocardial Oxygenation with Magnetic Resonance Imaging, UCLA Electronic Theses and Disssertations, 2016, 221 pages.

* cited by examiner

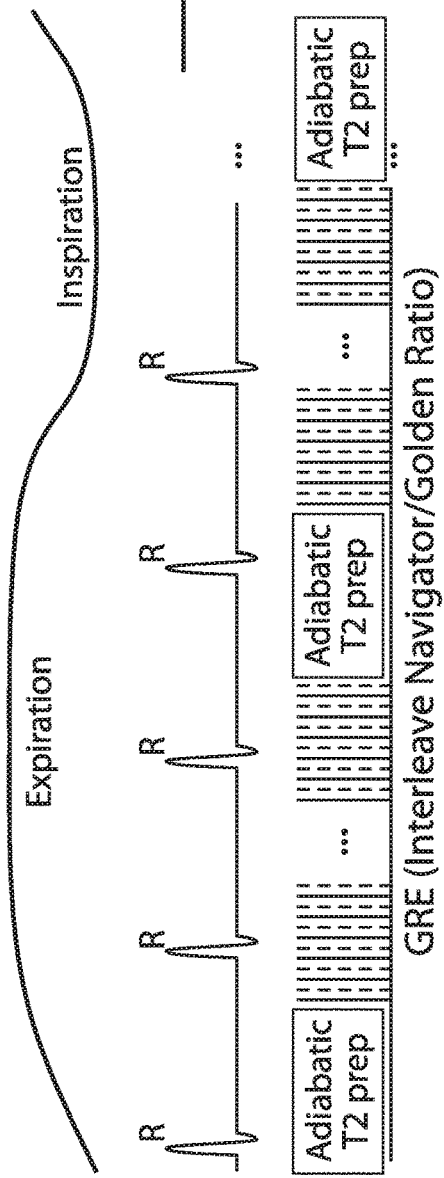
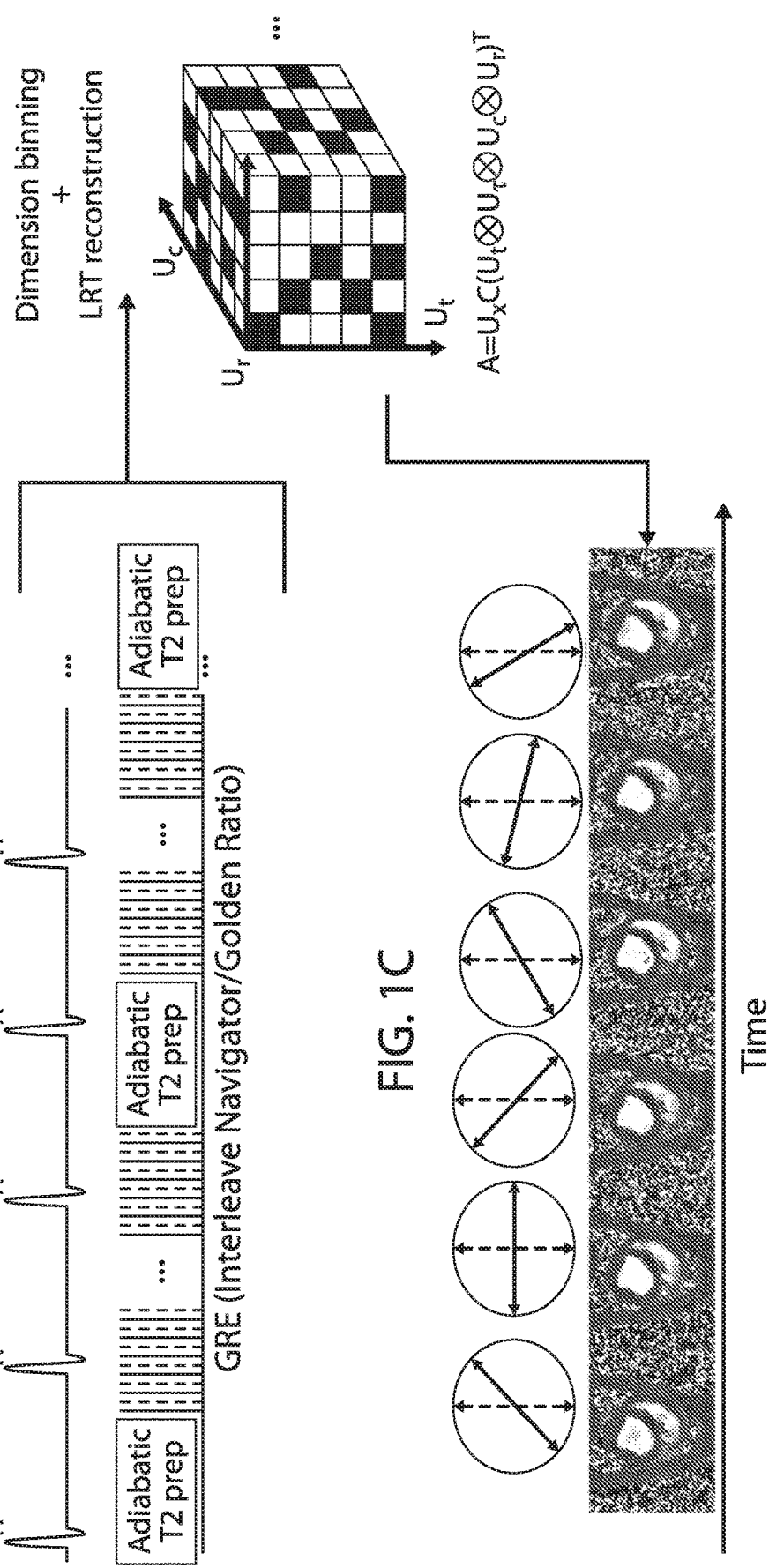
FIG. 1A
FIG. 1B
FIG. 1C

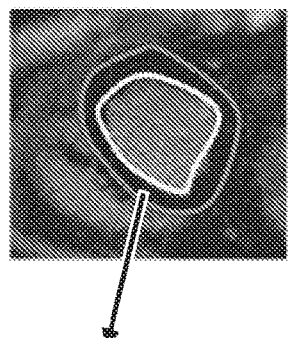
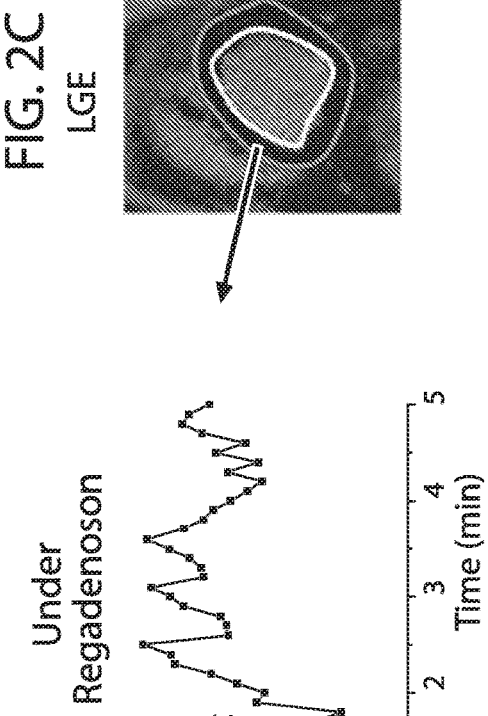
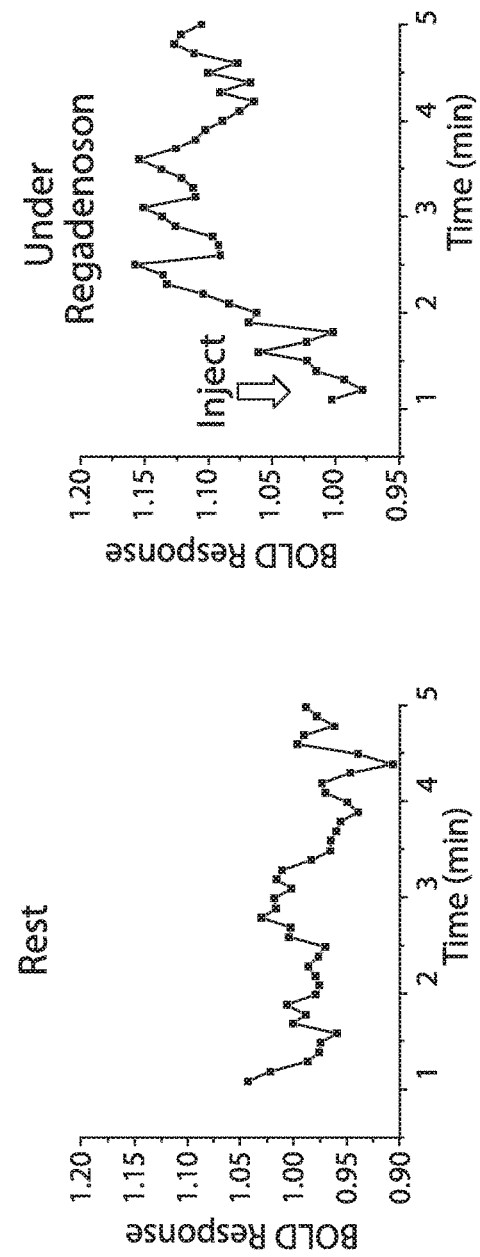
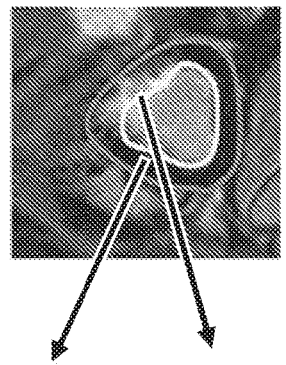
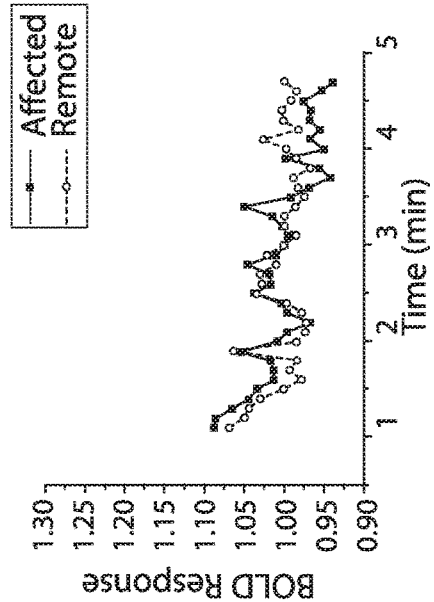
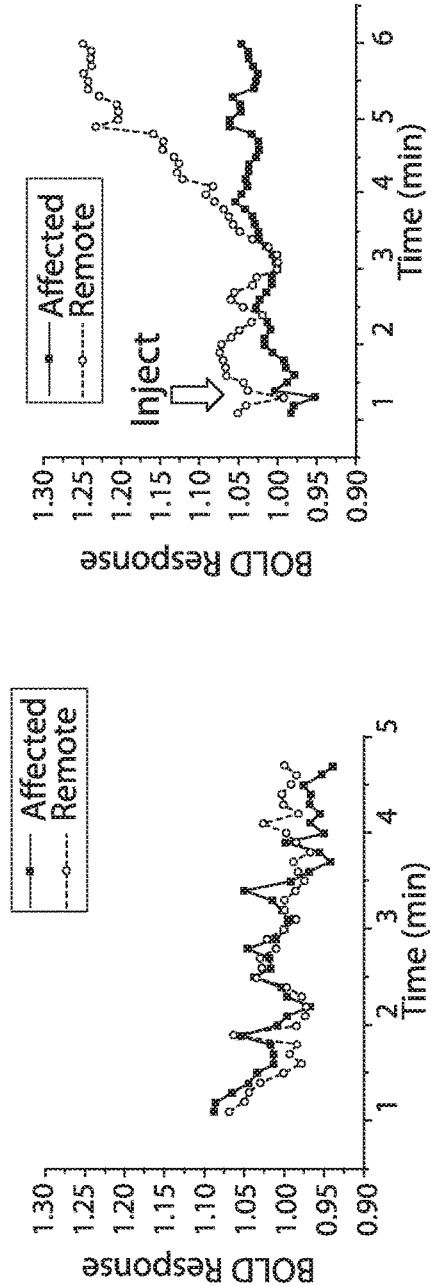

HIGHLY-TIMED RESOLVED MYOCARDIAL BLOOD-OXYGEN-LEVEL-DEPENDENT MAGNETIC RESONANCE IMAGING

CROSS-REFERENCE TO RELATED APPLICATION

This application is a National Phase of International Application No. PCT/US2019/029316, filed Apr. 26, 2019, which designated the U.S. and that International Application was published under PCT Article 21(2) in English, which also includes a claim of priority under 35 U.S.C § 119(e) to U.S. Provisional Patent Application No. 62/662,869 filed on Apr. 26, 2018, which is incorporated herein by reference in its entirety.

STATEMENT REGARDING FEDERALLY SPONSORED RESEARCH OR DEVELOPMENT

This invention was made with government support under Grant No. HL091989 awarded by National Institutes of Health. The government has certain rights in the invention.

FIELD OF THE INVENTION

The invention relates to cardiovascular imaging, particularly cardiovascular imaging under cardiac stress test for diagnosing and/or prognosing various cardiovascular diseases.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Coronary vasodilation and the ensuing myocardial hyperemia following the administration of a provocative stressor is a dynamic process. However, established perfusion methods are confounded by contrast accumulation and lack the temporal resolution to accurately evaluate the process. Blood Oxygen Level Dependent Cardiovascular Magnetic Resonance (BOLD CMR) imaging is an emerging method for monitoring myocardial perfusion without contrast agents, but the current methods are slow.

Thus there is a need in the art for cardiovascular imaging methods that overcome the limitations of known methods.

SUMMARY OF THE INVENTION

The following embodiments and aspects thereof are described and illustrated in conjunction with compositions and methods which are meant to be exemplary and illustrative, not limiting in scope.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging; wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a diagnosis of cardiovascular disease in the subject.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a diagnosis of cardiovascular disease in the subject.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a diagnosis of cardiovascular disease in the subject.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 1A-FIG. 1C depicts in accordance with various embodiments of the invention. A schematic of the image acquisition and reconstruction protocol is shown. FIG. 1A shows a continuous GRE sequence with adiabatic T2 preparation and golden-ratio radial trajectory (solid lines and solid arrows). The radial trajectory lines were interleaved with navigator signal (dashed lines and dashed arrows, 0° radial angle). The lines were sorted into respective dimensions (cardiac motion ($U_c$), respiratory motion ($U_r$), T1 recovery time ($U_t$), and time after excitation ($U_t$)) and reconstructed using a LRT framework plotted in FIG. 1B. The Data completion algorithm were used to recover the missing navigators and reconstruct the beat by beat BOLD images. A representative set of beat by beat reconstructed BOLD images are presented in FIG. 1C.

FIG. 2A-FIG. 2F depicts in accordance with various embodiments of the invention, dynamics of BOLD response at rest and under the influence of regadenoson. Representative results from an intact animal are presented in FIG. 2A-FIG. 2C. BOLD response was relatively flat (fluctuated within +/−5%) throughout the measurement at rest (FIG. 2A), but peaks at 2-3 minutes after regadenoson injection to 10-15% and then plateaus after 4 minutes of injection (FIG. 2B). FIG. 2C shows the corresponding LGE image (with no evidence of infarction) of the slice where BOLD response were measured. Representative results from an animal with chronic MI are shown in FIG. 2D-FIG. 2F. BOLD response was relatively flat in Remote and Affected territories at rest (FIG. 2D). However, under the influence of regadenoson (FIG. 2E), the BOLD response remained flat in Affected myocardium, while there was a delayed but rising BOLD response in Remote myocardium peaking at approximately 5 minutes was observed (FIG. 2E). The corresponding LGE image (with evidence of infarction) of the slice and where BOLD responses were measured are shown in FIG. 2F.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, NY 2006); Smith, March's Advanced Organic Chemistry Reactions, Mechanisms and Structure 7th ed., J. Wiley & Sons (New York, NY 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments, the numbers expressing quantities of ingredients, properties such as concentration, reaction conditions, conditions, time, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

"BOLD" as used herein refers to blood-oxygen-level dependence.

Blood Oxygen Level Dependent Cardiovascular Magnetic Resonance (BOLD CMR) and Blood Oxygen Level Dependent Magnetic Resonance Imaging (BOLD MRI) are used interchangeably herein.

As used herein, the terms "treat," "treatment," "treating," or "amelioration" when used in reference to a symptom, disease, disorder or disease condition, refer to both therapeutic treatment and prophylactic or preventative measures, wherein the object is to reverse, alleviate, ameliorate, inhibit, lessen, slow down or stop the progression or severity of a symptom, disease, disorder or disease condition. The term "treating" includes reducing or alleviating at least one adverse effect or symptom of a disease, disorder, or disease condition. Treatment is generally "effective" if one or more symptoms or clinical markers are reduced. Alternatively, treatment is "effective" if the progression of a symptom, disease, disorder or disease condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the symptom, disease, disorder, disease condition even if the treatment is ultimately unsuccessful. Those in need of treatment include those already with the symptom, disease, disorder, or disease condition as well as those prone to have the symptom, disease, disorder, or disease condition or those in whom the symptom, disease, disorder, or disease condition is to be prevented.

Non-limiting examples of treatments or therapeutic treatments include at least one selected from pharmacological therapies, biological therapies, interventional surgical treatments, and combinations thereof. Non-limiting examples of therapeutic treatments include any one or more of coronary revascularization through stenting, coronary bypass grafting, or medical therapy, or combinations thereof. Non-limiting examples of medical therapies include statins, LDL lowering, beta blockers, ACE inhibitors, aspirin, etc. or combinations thereof. In some embodiments, the treatment is a treatment for cardiovascular disease. In some embodiments, the treatment is a treatment for a symptom of cardiovascular disease. In some embodiments, the therapeutic treatment is a therapeutic treatment for cardiovascular disease. In some embodiments, the therapeutic treatment is a therapeutic treatment for a symptom of cardiovascular disease. In some embodiments, the method further comprises administering a treatment for cardiovascular disease to the subject. In some embodiments, the method further comprises administering a treatment for a symptom of cardiovascular disease to the subject.

The term "preventative treatment" means maintaining or improving a healthy state or non-diseased state of a healthy subject or subject that does not have a disease, symptom, disorder, or disease condition. The term "preventative treatment" also means to prevent or to slow the appearance of symptoms associated with a symptom, disease condition, disease, or disorder. The term "preventative treatment" also means to prevent or slow a subject from obtaining a symptom, disease condition, disease, or disorder.

"Beneficial results" or "desired results" may include, but are in no way limited to, lessening or alleviating the severity of the symptom, disease, disorder or disease condition; preventing the symptom, disease, disorder, or disease condition from worsening; curing the symptom, disease, disorder, or disease condition; preventing the symptom, disease, disorder, or disease condition from developing; lowering the chances of a patient developing the symptom, disease, disorder, or disease condition; decreasing morbidity and mortality; and prolonging a patient's life or life expectancy. As non-limiting examples, "beneficial results" or "desired results" may be alleviation of one or more symptom(s), diminishment of extent of the deficit, stabilized (i.e., not worsening) state of a cardiovascular disease, delay or slowing of a cardiovascular disease, and amelioration or palliation of symptoms associated with a cardiovascular disease.

The term "disease" refers to an abnormal condition affecting the body of an organism. For example, the disease or abnormal condition may result from a pathophysiological response to external or internal factors.

The term "disorder" refers to a functional abnormality or disturbance. For example, a disorder may be a disruption of the disease to the normal or regular functions in the body or a part of the body.

The term "disease condition" refers to an abnormal state of health that interferes with the usual activities of feeling and wellbeing.

The term "normal condition" or "healthy condition" refers to a normal state of health.

The term "healthy state" or "normal state" means that the state of a subject (e.g., biological state or health state, etc.) is not abnormal and does not comprise a disease, disease condition, or disorder.

A "healthy subject" or "normal subject" is a subject that does not have a disease, disease condition, or disorder.

Examples of diseases and disease conditions, as used herein may include cardiovascular diseases and/or cardiovascular disease conditions but are in no way limited to cardiovascular diseases and/or cardiovascular disease conditions. Cardiovascular diseases are a class of diseases that involve the heart or blood vessels. Non-limiting examples of cardiovascular disease include: coronary artery disease, coronary heart disease, ischemic heart disease (IHD), cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease (PAD).

As used herein, the term "administering," refers to the placement of a therapeutic agent or a treatment as disclosed herein into a subject by a method or route which results in at least partial localization of the therapeutic agent or treatment at a desired site. "Route of administration" may refer to any administration pathway known in the art, including but not limited to aerosol, nasal, via inhalation, oral, anal, intra-anal, peri-anal, transmucosal, transdermal, parenteral, enteral, topical or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the therapeutic agent or treatment may be in the form of solutions or suspensions for infusion or for injection, or as lyophilized powders. Via the enteral route, the therapeutic agent or treatment can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the therapeutic agent or treatment can be in the form of aerosol, lotion, cream, gel, ointment, suspensions, solutions or emulsions. In accordance with the present invention, "administering" can be self-administering. For example, it is considered as "administering" that a subject consumes a therapeutic agent or treatment as disclosed herein.

"Diagnostic" means identifying the presence or nature of a disease condition, disease, or disorder and includes identifying patients who are at risk of developing a specific disease condition, disease or disorder. In various embodiments, diagnostic assays, methods, and techniques differ in their sensitivity and specificity. In some embodiments, the "sensitivity" of a diagnostic assay, method, or technique is the percentage of diseased individuals who test positive (percent of "true positives"). In some embodiments, diseased individuals not detected by the assay, method, or technique are "false negatives." In some embodiments, subjects who are not diseased and who test negative in the assay, method, or technique are termed "true negatives." In some embodiments, the "specificity" of a diagnostic assay, method, or technique is 1 minus the false positive rate, where the "false positive" rate is defined as the proportion of those without the disease who test positive. While a particular diagnostic assay, method, or technique may not provide a definitive diagnosis of a disease condition, a disease, or a disorder, it suffices if the assay, method, or technique provides a positive indication that aids in diagnosis.

By "at risk of" is intended to mean at increased risk of, compared to a reference, compared to a normal subject, or compared to a control group, e.g. a patient population. Thus a subject carrying a particular marker or having a particular symptom may have an increased risk for a specific disease condition, disease or disorder, and be identified as needing further testing. "Increased risk" or "elevated risk" mean any statistically significant increase in the probability, e.g., that the subject has the disorder, disease, or disease condition. In some embodiments the risk is increased by at least 10% over the control group with which the comparison is being made. In some embodiments, the risk is increased by at least 20% over the control group with which the comparison is being made. In some embodiments, the risk is increased by at least 50% over the control group with which the comparison is being made.

The terms "detection", "detecting" and the like, may be used in the context of detecting a symptom, detecting a disease condition, detecting a disease, or detecting a disorder (for example, when positive assay or test results are obtained).

The term "diagnosis," or "dx," refers to the identification of the nature and cause of a certain phenomenon. As used herein, a diagnosis typically refers to a medical diagnosis, which is the process of determining which disease, disorder or disease condition explains a symptoms and signs. In some embodiments, a diagnostic procedure, often a diagnostic test or assay, technique, or method, can be used to provide a diagnosis. A diagnosis can comprise detecting the presence of a disease or disorder, or disease condition.

The term "prognosis," or "px," as used herein refers to predicting the likely outcome of a current standing. For example, a prognosis can include the expected duration and course of a symptom, disease condition, disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

"Sample" is used herein in its broadest sense. The term "biological sample" as used herein denotes a sample taken or isolated from a biological organism. A sample or biological sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Exemplary biological samples include, but are not limited to, cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample is a tissue or tissue sample. In some embodiments, the sample is a biological sample.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In some embodiments, the subject is a human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a symptom, disease, disorder, or disease condition in need of treatment (e.g., a cardiovascular disease) or one or more complications related to the symptom, disease, disorder, or disease condition, and optionally, have already undergone treatment for the symptom, disease, disorder, or disease condition or the one or more complications related to the symptom, disease, disorder, or disease condition. Alternatively, a subject can also be one who has not been previously diagnosed as having a symptom, disease, disorder, or disease condition or one or more complications related to the symptom, disease, disorder, or disease condition. For example, a subject can be one who exhibits one or more risk factors for a symptom, disease, disorder, or disease condition or one or more complications related to the symptom, disease, disorder, or disease condition or a subject who does not exhibit risk factors. A "subject in need" of treatment for a particular symptom, disease, disorder, or disease condition can be: a subject suspected of having that symptom, disease, disorder, or disease condition; a subject diagnosed as having that symptom, disease, disorder, or disease condition; a subject already treated or being treated for that symptom, disease, disorder, or disease condition; a subject not treated for that symptom, disease, disorder, or disease condition; or a subject at risk of developing that symptom, disease, disorder, or disease condition.

The term "statistically significant" or "significantly" refers to statistical evidence that there is a difference. It is defined as the probability of making a decision to reject the null hypothesis when the null hypothesis is actually true. The decision is often made using the p-value.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, "remote territory" means normal myocardial territory that is not affected by cardiovascular disease.

As used herein, "affected territory" means abnormal myocardial territory that is affected by cardiovascular disease.

As used herein, "motion-corrected" means that the raw imaging data (e.g., raw MRI data) that is acquired in the presence of cardiac and respiratory motion is retrospectively processed post imaging to remove the motion information which would otherwise appear as image artifacts and confound the interpretation.

As used herein, "registration" or "registered" or "registering" means that multiple images are acquired and the image with least motion (reference image) is first identified and then the remaining acquisitions are related back to the reference image to alter the image features with motion so as to map the images with motion to derive motion-corrected images. The process of mapping back to the reference images is referred to as registration herein.

As used herein, "rest" means before administration of a stress agent.

As used herein, "rest image" means an image obtained before administration of a stress agent.

As used herein, "stress" means after administration of a stress agent.

As used herein, "stress image" means an image obtained after administration of a stress agent.

As used herein, "ms" means milliseconds.

As used herein, "min" or "mins" means minute or minutes.

As used herein, "bpm" means beats per minute.

As used herein, "(ml/min/g)" means (milliliter/minute/gram).

As used herein, "(ml/mg/min)" means (milliliter/milligram/minute).

As used herein, "(mg/kg/min)" means (milligram/kilogram/minute).

As used herein, "vascular reactivity" means the capacity of blood vessels to respond to an endogenous or exogenous substance with an increase in blood flow.

As used herein, "hyperemia response" means increased blood flow relative to resting conditions.

As used herein, "myocardial perfusion reserve" is the ratio of blood flow at peak hyperemia to blood flow at rest.

As used herein, "perfusion" means blood flow through the vasculature of an organ.

As used herein, "myocardial perfusion" means blood flow through the vasculature of the heart muscle.

As used herein, "beat-to-beat heartbeat time interval" means the amount of time that lapses between an initial heartbeat of interest and a following heartbeat of interest, wherein the following heartbeat of interest is immediately after the initial heartbeat of interest. In other words, in a beat-to-beat heartbeat time interval there are no other heartbeats between the initial heartbeat of interest and the following heartbeat of interest. For the beat-to-beat heartbeat time interval, the time between the initial heartbeat of interest and the following heartbeat of interest can vary for individual subjects according to a variety of factors including but not limited to age, sex, weight, height, state of health, rest state, stress state, administration of stress agent, type of stress agent administered, etc.

In some embodiments, the beat-to-beat heartbeat time interval consists of two heartbeats. In some embodiments, the beat-to-beat heartbeat time interval consists essentially of two heartbeats. In some embodiments, the beat-to-beat heartbeat time interval comprises two heartbeats.

As used herein, "multiple heartbeat time interval" is defined as the amount of time that lapses between an initial heartbeat of interest and a following heartbeat of interest, wherein the following heartbeat of interest is not immediately after the initial heartbeat of interest. In other words, in a multiple heartbeat time interval there is at least one additional heartbeat between the initial heartbeat of interest and the following heartbeat of interest. For the multiple heartbeat time interval, the time between the initial heartbeat of interest and the following heartbeat of interest can vary for individual subjects according to a variety of factors including but not limited to age, sex, weight, height, state of health, rest state, stress state, administration of stress agent, type of stress agent administered, etc.

In some embodiments, a multiple heartbeat time interval comprises up to 3000 heartbeats. In some embodiments, a multiple heartbeat time interval comprises up to 600 heartbeats. In some embodiments, a multiple heartbeat time interval comprises 3000 to 3 heartbeats, 2000 to 3 heartbeats, 1000 to 3 heartbeats, 900 to 3 heartbeats, 800 to 3 heartbeats, 700 to 3 heartbeats, 600 to 3 heartbeats, 500 to 3 heartbeats, 400 to 3 heartbeats, 300 to 3 heartbeats, 200 to 3 heartbeats, 100 to 3 heartbeats, 90 to 3 heartbeats, 80 to 3 heartbeats, 70 to 3 heartbeats, 60 to 3 heartbeats, 50 to 3 heartbeats, 40 to 3 heartbeats, 30 to 3 heartbeats, 20 to 3 heartbeats, or 10 to 3 heartbeats. In some embodiments, the multiple heartbeat time interval comprises at least 3 heartbeats.

Coronary vasodilation and the ensuing myocardial hyperemia following the administration of a provocative stressor is a dynamic process. Noninvasive assessment of this process can provide important insights into the vasomotor activity of coronary vessels, which is known to be impaired in numerous pathologies that affect the heart. Current methods for ascertaining myocardial perfusion rely on monitoring the accumulation and passage of exogenous contrast agents. However, slow clearance of these contrast agents limits true assessment of time-resolved changes in blood flow in response to a coronary vasodilator. A subtle consequence of this is reflected in the empirical delay set by the operator between the start of the vasodilator infusion and imaging data acquisition in first-pass perfusion (FPP) exams, which can compromise the capture of peak coronary vasodilation in some subjects. Hence, FPP approaches effectively limit blood flow assessments to two physiological states: one at rest; and another at some presumed peak vasodilatory state. Cardiac BOLD MRI is an emerging method for probing myocardial perfusion without contrast agents. However, current Blood Oxygen Level Dependent Cardiovascular Magnetic Resonance (BOLD CMR) techniques are slow; thus, they do not have the temporal resolution to report on the vasodilatory changes in the heart that occur at a much faster time scale. Moreover, they are sensitive to breathing motion and have low tolerance to rapidly varying heart rates (R-R intervals) following the administration of stress agents. To overcome these limitations and to enable rapid time-resolved assessment of myocardial perfusion, we developed a non-ECG-gated, free breathing, beat-to-beat, respiratory and cardiac phase-resolved, T2-based BOLD CMR sequence at 3T using a low rank tensor (LRT) framework. The method generates T2 BOLD images at any time point during the period of interest. It provides an opportunity to continuously monitor the BOLD changes during cardiac stress exam. In addition, the method is insensitive to breathing motion and heart rate variability, which can significantly reduce patient discomfort and increase image reliability. Specifically, we tested whether the myocardial perfusion dynamics can be captured using the proposed method in intact animals before and after the administration of regadenoson, a commonly used coronary vasodilator. We also applied the proposed technique for the assessment of dynamical changes in regional perfusion in an animal model with coronary disease.

In various embodiments, the proposed cardiac BOLD MRI approach was developed based on an LRT formalism (acquisition and reconstruction). It is composed of 3 parts: (i) adiabatic T2 preparation that is repeated at a fixed interval to ensure consistent T2 weighting; (ii) repeat acquisition of a set of central k-space lines with GRE readout every other TR to serve as respiratory and cardiac navigators for reconstruction; and (iii) interleaving of a set of golden-ratio radial GRE readout lines with the navigator lines serving as LRT training data. A high-dimensional cardiac image space (cardiac motion (Uc), respiratory motion (Ur), T1 recovery time (Ut), and time after excitation (Ut)) as a low-rank tensor that is partially separable was modeled. The complete tensors of all subspaces were recovered from the frequently (every 6 ms) sampled navigator signal using LRT completion. Subsequently cardiac and respiratory phased-resolved, beat-to-beat cardiac BOLD images were reconstructed. The data acquisition and reconstruction schemes are illustrated in FIG. 1 This was tested in animals with and without myocardial infarction. Sequence parameters were: scan time: 6 mins, delay between T2prep=800 ms; TE (T2prep time)=60 ms; GRE readout (TE/TR=1.4/3.3 ms, flip angle=12°, FOV=270×270 mm2, in-plane resolution: 1.7×1.7 mm2, 1 slice of thickness: 6 mm).

Vascular reactivity may be monitored by characterization of myocardial perfusion reserve, which is defined as a ratio of myocardial perfusion at stress to myocardial perfusion at rest. In healthy subjects the ratio may vary from 2:1 to 6:1. The ratio diminishes with disease. A decrease in this ratio to 2:1 or below from the healthy level is considered clinically significant and indicative of poor vascular reactivity. Also, vascular reactivity may be monitored via differential absolute perfusion, which may be obtained using imaging methods such as first pass perfusion, SPECT/PET, CT perfusion or echocardiography in units of ml/sec/g (milliliter/second/gram) of tissue.

A coronary vasoreactive response (or cardiac stress response or hyperemic response) means a type and/or quantum of vasoreactive response elicited by cardiac stress testing (e.g. exercise or administration of a hyperemic drug) as demonstrable in an imaging study using one or more diagnostic imaging parameters of the type suitable to diagnose coronary vascular disease. For example, with respect to PET and SPECT, a normal response would be considered a four to five fold increase in blood flow. With respect to BOLD MRI imaging, a 10-12% increase in BOLD signal would be considered normal.

Disease-associated responses are those which are not normal in varying significant degrees. As evidence of disease, benchmarks may be adopted to categorize differences which represent a clear-cut diagnosis or a progression of disease that warrants greater follow-up or more proactive treatment. A benchmark, may be for example, a less than two-fold increase in blood flow as measured by PET or SPECT (typically measured in ml. of blood/min/gm of tissue). Accordingly, a benchmark represents a change from a value that clinicians describe as "normal". For example, a change from "normal" which is at least statistically significant, and optionally is also comparable to a standard for cardiac stress testing adopted by clinicians with respect to inducing stress, represents a clear-cut benchmark for using exercise or a hyperemic drug as a vasoactive stress stimulus.

The inventor's approach improves the image quality of BOLD images specifically during stress. The inventors achieve this by imaging the cardiovascular system in the subject after administration of the stress agent over a period of time to obtain a series of stress images and stress data, wherein the stress images and stress data are obtained at a time interval between each stress image, wherein the time interval between each stress image is a beat-to-beat heartbeat interval. Notably during this period, even if the heart rates are high, MRI acquisition could be tuned adequately to capture myocardial hyperemia with markedly reduced image artifacts. This also improves patient comfort since cardiac stress is induced outside the MRI chamber and the imaging time is reduced.

Various Non-Limiting Embodiments of the Present Invention

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a diagnosis of cardiovascular disease in the subject.

In various embodiments, the present invention provides a method for diagnosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a diagnosis of cardiovascular disease in the subject.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a diagnosis of cardiovascular disease in the subject.

In various embodiments, the present invention provides a method for diagnosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a diagnosis of cardiovascular disease in the subject.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a diagnosis of cardiovascular disease in the subject.

In various embodiments, the present invention provides a method for diagnosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a diagnosis of cardiovascular disease in the subject.

In various embodiments, the present invention provides method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a diagnosis of cardiovascular disease in the subject.

In various embodiments, the present invention provides method for diagnosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a diagnosis of cardiovascular disease in the subject.

In various embodiments, the present invention provides a method for imaging at least a portion of a cardiovascular system in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system, thereby imaging at least a portion of a cardiovascular system in a subject.

In various embodiments, the present invention provides a method for imaging at least a portion of a cardiovascular system in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system, thereby imaging at least a portion of a cardiovascular system in a subject.

In various embodiments, the present invention provides a method for identifying and/or assessing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of and/or an assessment of cardiovascular disease in the subject.

In various embodiments, the present invention provides a method for identifying and/or assessing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of and/or an assessment of cardiovascular disease in the subject.

In various embodiments, the present invention provides a method for detecting cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of cardiovascular disease in the subject.

In various embodiments, the present invention provides a method for detecting cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of cardiovascular disease in the subject.

In various embodiments, the present invention provides a method for prognosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a prognosis of cardiovascular disease in the subject.

In various embodiments, the present invention provides a method for prognosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a prognosis of cardiovascular disease in the subject.

In various embodiments the present invention provides a method for determining progression of cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of progression of cardiovascular disease in the subject.

In various embodiments the present invention provides a method for determining progression of cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of progression of cardiovascular disease in the subject.

In various embodiments, the present invention provides a method for assessing and/or determining the risk of developing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of an increased risk of the subject developing cardiovascular disease.

In various embodiments, the present invention provides a method for assessing and/or determining the risk of developing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another so as to determine a response to oxygenation and blood flow in the at least a portion of the subject's cardiovascular system; and (f) comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is indicative of an increased risk of the subject developing cardiovascular disease.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress over a second period of time so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a diagnosis of cardiovascular disease in the subject.

In various embodiments, the present invention provides a method for diagnosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a diagnosis of cardiovascular disease in the subject.

In various embodiments, the present invention provides a method for identifying and/or assessing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of and/or an assessment of cardiovascular disease in the subject.

In various embodiments, the present invention provides a method for identifying and/or assessing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of and/or an assessment of cardiovascular disease in the subject.

In various embodiments, the present invention provides a method for detecting cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of cardiovascular disease in the subject.

In various embodiments, the present invention provides a method for detecting cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of cardiovascular disease in the subject.

In various embodiments, the present invention provides a method for prognosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a prognosis of cardiovascular disease in the subject.

In various embodiments, the present invention provides a method for prognosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a prognosis of cardiovascular disease in the subject.

In various embodiments, the present invention provides a method for determining progression of cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of progression of cardiovascular disease in the subject.

In various embodiments, the present invention provides a method for determining progression of cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of progression of cardiovascular disease in the subject.

In various embodiments, the present invention provides a method for assessing and/or determining the risk of developing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of an increased risk of the subject developing cardiovascular disease.

In various embodiments, the present invention provides a method for assessing and/or determining the risk of developing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, (d) registering the stress images to at least one of the rest images so as to obtain a plurality of motion-corrected images of the at least a portion of the subject's cardiovascular system; and (e) comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is indicative of an increased risk of the subject developing cardiovascular disease.

In various embodiments, the present invention provides a method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a diagnosis of cardiovascular disease in the subject.

In various embodiments, the present invention provides a method for diagnosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a diagnosis of cardiovascular disease in the subject.

In various embodiments, the present invention provides a method for identifying and/or assessing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of and/or an assessment of cardiovascular disease in the subject.

In various embodiments, the present invention provides a method for identifying and/or assessing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of and/or an assessment of cardiovascular disease in the subject.

In various embodiments, the present invention provides a method for detecting cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of cardiovascular disease in the subject.

In various embodiments, the present invention provides a method for detecting cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of cardiovascular disease in the subject.

In various embodiments, the present invention provides a method for prognosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a prognosis of cardiovascular disease in the subject.

In various embodiments, the present invention provides a method for prognosing cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a prognosis of cardiovascular disease in the subject.

In various embodiments, the present invention provides a method for determining progression of cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of progression of cardiovascular disease in the subject.

In various embodiments, the present invention provides a method for determining progression of cardiovascular disease in a subject, comprising: (a) imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of progression of cardiovascular disease in the subject.

In various embodiments, the present invention provides a method for assessing and/or determining the risk of developing cardiovascular disease in a subject, comprising: imaging at least a portion of the subject's cardiovascular system at rest so as to obtain a rest image and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of an increased risk of the subject developing cardiovascular disease.

In various embodiments, the present invention provides a method for assessing and/or determining the risk of developing cardiovascular disease in a subject, comprising: (a) imaging at least a portion of the subject's cardiovascular system at rest so as to obtain a rest image and rest data of the at least a portion of the subject's cardiovascular system, wherein imaging the at least a portion of the subject's cardiovascular system at rest comprises operating imaging equipment and performing an imaging technique, wherein the rest images and rest data are obtained at a time interval between each rest image, and wherein the time interval between each rest image is selected from a beat-to-beat heartbeat time interval, a multiple heartbeat time interval, and combinations thereof; (b) administering an effective amount of at least one stress agent to the subject, wherein the stress agent is at least one vasodilator; (c) imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating imaging equipment and performing an imaging technique, wherein the stress images and stress data are obtained at a time interval between each stress image, and wherein the time interval between each stress image is selected from a beat-to-beat heartbeat time interval, a multiple heartbeat time interval, and combinations thereof; (d) registering the stress images to at least one of the rest images so as to obtain a plurality of motion-corrected images of the at least a portion of the subject's cardiovascular system; (e) comparing the plurality of motion corrected images of the at least a portion of the subject's cardiovascular system to one another to determine vascular reactivity in the at least a portion of the subject's cardiovascular system; and (f) comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is indicative of an increased risk of the subject developing cardiovascular disease.

In various embodiments, the present invention provides a method of imaging a subject's cardiovascular system. The method may consist of or may consist essentially of or may comprise: (a) imaging the subject's cardiovascular system at rest; (b) administering a stress agent to the subject; and (c) imaging the subject's cardiovascular system after administering the stress agent. In various embodiments, the stress agent is at least one vasodilator. In various embodiments, the method further comprises assessing vascular activity based on the imaging results at rest and after administering the vasodilator. For non-limiting examples, hyperemia response and/or myocardial perfusion reserve can be calculated and/or measured and/or determined from the imaging results at rest and after administering the vasodilator. In various embodiments, abnormal vascular activity indicates the presence of a cardiovascular disease or likelihood to develop a cardiovascular disease. In some embodiments, decreased vascular activity indicates the presence of a cardiovascular disease or likelihood to develop a cardiovascular disease. In other embodiments, increased vascular activity indicates the presence of a cardiovascular disease or likelihood to develop a cardiovascular disease.

In some embodiments, the method further comprises diagnosing the subject as having a cardiovascular disease. In some embodiments, the method further comprises prognosing the subject as being likely to develop a cardiovascular disease. In some embodiments, the method further comprises prognosing the subject as having a higher probability of developing a cardiovascular disease as compared to a healthy subject. In various embodiments, the diagnosis and/or prognosis is based on the imaging results at rest and after administering the stress agent. In some embodiments, the method further comprises administering a treatment for cardiovascular disease to the subject, thereby treating the cardiovascular disease.

In some embodiments, wherein imaging at least a portion of the subject's cardiovascular system at rest is over a first period of time.

In some embodiments, wherein the first period of time is selected from the group consisting of at least 10 hours, at least 5 hours, at least 2 hours, at least 1 hour, at least 30 minutes, at least 15 minutes, at least 10 minutes, at least 5 minutes, and at least 1 minute.

In some embodiments, wherein the first period of time is selected from the group consisting of up to 10 hours, up to 5 hours, up to 2 hours, up to 1 hour, up to 30 minutes, up to 15 minutes, up to 10 minutes, and up to 1 minute.

In some embodiments, wherein the time interval between each rest image is a multiple heartbeat time interval, wherein the multiple heartbeat time interval is selected from the group consisting of up to 20 minutes, up to 15 minutes, up to 10 minutes, up to 9 minutes, up to 8 minutes, up to 7 minutes, up to 6 minutes, up to 5 minutes, up to 4 minutes, up to 3 minutes, up to 2 minutes, up to 1 minute, up to 45 seconds, up to 30 seconds, up to 15 seconds, up to 10 seconds, and up to 2 seconds.

In some embodiments, the time interval between each rest image is a beat-to-beat heartbeat time interval.

In some embodiments, wherein imaging at least a portion of the subject's cardiovascular system at stress is after administration of the stress agent to the subject.

In some embodiments, wherein imaging at least a portion of the subject's cardiovascular system at stress is over a second period of time.

In some embodiments, wherein the second period of time is selected from the group consisting of at least 10 hours, at least 5 hours, at least 2 hours, at least 1 hour, at least 30 minutes, at least 15 minutes, at least 10 minutes, at least 5 minutes, and at least 1 minute.

In some embodiments, wherein the second period of time is selected from the group consisting of up to 10 hours, up to 5 hours, up to 2 hours, up to 1 hour, up to 30 minutes, up to 15 minutes, up to 10 minutes, and up to 1 minute.

In some embodiments, wherein the time interval between each stress image is a multiple heartbeat time interval, wherein the multiple heartbeat time interval is selected from the group consisting of up to 20 minutes, up to 15 minutes, up to 10 minutes, up to 9 minutes, up to 8 minutes, up to 7 minutes, up to 6 minutes, up to 5 minutes, up to 4 minutes, up to 3 minutes, up to 2 minutes, up to 1 minute, up to 45 seconds, up to 30 seconds, up to 15 seconds, and up to 10 seconds, and up to 2 seconds.

In some embodiments, the time interval between each stress image is a beat-to-beat heartbeat time interval.

In some embodiments, wherein the imaging of the at least a portion of the subject's cardiovascular system after administration of the stress agent is performed over a period of time, wherein the period of time is selected from the group consisting of at least 1 hour, at least 30 minutes, at least 15 minutes, at least 10 minutes, at least 5 minutes, and at least 1 minute.

In some embodiments, wherein the imaging of the at least a portion of the subject's cardiovascular system after administration of the stress agent is performed over a period of time, wherein the period of time is selected from the group consisting of up to 2 hours, up to 1 hour, up to 30 minutes, up to 15 minutes, and up to 10 minutes.

In some embodiments of the methods of the present invention, wherein the imaging the at least a portion of the subject's cardiovascular system at stress after administration of the stress agent so as to obtain a series of stress images and stress data of the at least a portion of the subject's cardiovascular system is performed about 0.1-0.5, 0.5-1, 1-5, 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after administering an effective amount of at least one stress agent to the subject, wherein the stress agent is at least one vasodilator.

In some embodiments of the methods of the present invention, wherein step (c) is performed about 0.1-0.5, 0.5-1, 1-5, 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b).

In some embodiments, the imaging can be performed continuously. In some embodiments, the imaging can be performed in a step-wise manner.

In various embodiments, the cardiovascular disease is coronary artery disease, coronary heart disease, ischemic heart disease (HID), cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, peripheral artery disease (PAD), infarcted myocardium, or a combination thereof. In various embodiments, the cardiovascular disease is coronary artery disease, coronary heart disease, ischemic heart disease (IHD), cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, peripheral artery disease (PAD), infarcted myocardium, or combinations thereof.

In various embodiments, the cardiovascular disease is infarcted myocardium. In various embodiments, the cardiovascular disease is ischemic heart disease (IHD). In various embodiments, the cardiovascular disease is myocardium affected by ischemic heart disease. In various embodiments, the cardiovascular disease is ischemic myocardium. In various embodiments, the cardiovascular disease is ischemic myocardium affected by coronary narrowing and microvascular disease.

In some embodiments, the portion of the subject's cardiovascular system is selected from the group consisting of a heart, a portion of a heart, at least one blood vessel, a portion of a blood vessel, and combinations thereof. In some embodiments, the portion of the heart is selected from a myocardium. In some embodiments, the blood vessel is selected from the group consisting of a vein, artery, capillary, and combinations thereof. In some embodiments, the artery is a coronary artery.

In various embodiments, the subject is a human. In various embodiments, the subject is a mammalian subject including but not limited to human, monkey, ape, dog, cat, cow, horse, goat, pig, rabbit, mouse and rat.

In various embodiments, the stress agent is at least one vasodilator.

In various embodiments, the vasodilator induces hyperemia. In various embodiments, hyperemia response is reduced or compromised in subjects with cardiovascular diseases as compared to healthy subjects. As a non-limiting example, coronary artery disease leads to narrowing of the small blood vessels that supply blood and oxygen to the heart, and hence is expected to reduce hyperemic response and the perfusion reserve.

In various embodiments, the vasodilator is a selective A2A adenosine receptor agonist. In some embodiments, the selective A2A adenosine receptor agonist is regadenoson, or a functional equivalent, analog, derivative or salt of regadenoson. In other embodiments, the selective A2A adenosine receptor agonist is binodenoson, or a functional equivalent, analog, derivative or salt of binodenoson. In still other embodiments, the selective A2A adenosine receptor agonist is apadenoson, or a functional equivalent, analog, derivative or salt of apadenoson. In some embodiments, the selective A2A adenosine receptor agonist is adenosine, or a functional equivalent, analog, derivative or salt of adenosine.

In various embodiments, the vasodilator is selected from regadenoson, binodenoson, apadenoson, and dipyridamole. In various embodiments, the vasodilator is selected from regadenoson, binodenoson, apadenoson, dipyridamole, and adenosine. In various embodiments the vasodilator is regadenoson. In various embodiments the vasodilator is binodenoson. In various embodiments the vasodilator is apadenoson. In various embodiments the vasodilator is dipyridamole. In various embodiments the vasodilator is adenosine. In various embodiments, the vasodilator is selected from the group consisting of regadenoson, binodenoson, apadenoson, dipyridamole, adenosine, and combinations thereof. In various embodiments, the vasodilator is selected from the group consisting of regadenoson, binodenoson, apadenoson, dipyridamole, adenosine, and a combination thereof.

Typical dosages of an effective amount of the vasodilator can be in their ranges recommended by the manufacturer where known vasodilators are used, and also as indicated to the skilled artisan by the responses in animal models or human subjects. Such dosages typically can be reduced by up to about an order of magnitude in concentration or amount without losing relevant biological activity. The actual dosage can depend upon the judgment of the physician, the condition of the patient, and the effectiveness of the imaging method based, for example, on the effectiveness observed in relevant and appropriate animal models. In various embodiments, the vasodilator may be administered once a day (SID/QD), twice a day (BID), three times a day (TID), four times a day (QID), or more, so as to administer an effective amount of the vasodilator to the subject, where the effective amount is any one or more of the doses described herein. In various embodiments, the vasodilator may be administered once, twice, three or more times.

In various embodiments, the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof. In various embodiments, the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

In various embodiments, the vasodilator is administered at a rate of about 0.07 mg/kg/min to about 0.28 mg/kg/min. In various embodiments, the vasodilator is administered at a rate of 0.07 mg/kg/min to 0.28 mg/kg/min. In various embodiments, the vasodilator is administered at 0.07 mg/kg/min to 0.28 mg/kg/min. In various embodiments, the vasodilator is administered at 0.07 to 0.28, 0.07 to 0.27, 0.07 to 0.26, 0.07 to 0.25, 0.07 to 0.24, 0.07 to 0.23, 0.07 to 0.22, 0.07 to 0.21, 0.07 to 0.20, 0.07 to 0.19, 0.07 to 0.18, 0.07 to 0.17, 0.07 to 0.16, 0.07 to 0.15, 0.07 to 0.14, 0.07 to 0.13, 0.07 to 0.12, 0.07 to 0.11, 0.07 to 0.10, 0.07 to 0.09, or 0.07 to 0.08 mg/kg/min. In various embodiments, the vasodilator is administered at 0.07 to 0.28, 0.08 to 0.28, 0.09 to 0.28, 0.10 to 0.28, 0.11 to 0.28, 0.12 to 0.28, 0.13 to 0.28, 0.14 to 0.28, 0.15 to 0.28, 0.16 to 0.28, 0.17 to 0.28, 0.18 to 0.28, 0.19 to 0.28, 0.20 to 0.28, 0.21 to 0.28, 0.22 to 0.28, 0.23 to 0.28, 0.24 to 0.28, 0.25 to 0.28, 0.26 to 0.28, or 0.27 to 0.28 mg/kg/min. In some embodiments, kg is kg body weight, and mg is the amount of vasodilator.

In accordance with the invention, the vasodilator may be administered using the appropriate modes of administration, for instance, the modes of administration recommended by the manufacturer for each of the vasodilator. In accordance with the invention, various routes may be utilized to administer the vasodilator of the claimed methods, including but not limited to intratumoral, intravascular, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, the vasodilator is administered intravascularly, intravenously, or intraarterially. In various embodiments, the vasodilator is administered intravascularly, intravenously, intraarterially, or intracoronary. In some embodiments, the vasodilator is administered by inhalation.

In some embodiments, the vasodilator is administered in a stepwise manner. In some embodiments, the vasodilator is administered in a block-wise manner. In some embodiments, the vasodilator is administered in a stepwise manner or a block-wise manner.

In various embodiments, the vasodilator is administered as a single bolus. In various embodiments, the single bolus is injected intravascularly, intravenously, or intraarterially to the subject. In various embodiments, the single bolus is injected intravascularly, intravenously, intraarterially, or intracoronary. In some embodiments, the single bolus is injected intravenously to the subject. In various embodiments, the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

In various embodiments, the vasodilator is administered as a continuous infusion. In various embodiments, the vasodilator can be administered as a continuous infusion using a programmable continuous infusion ambulatory pump or iv infusion bags or any other means known in the art. In various embodiments, the exact dosage range of the vasodilator administered as a continuous infusion will depend on the age, body weight, and/or condition of the subject being treated. As a non-limiting example, continuous infusion of adenosine is typically <240 mg/kg/min (this is two times the current dose). As a non-limiting example, continuous infusion with regadenoson should be <0.4 mg (accumulated dose over 30 minutes).

In various embodiments, the vasodilator is carbon dioxide ($CO_2$). In various embodiments, the vasodilator comprises carbon dioxide ($CO_2$).

In various embodiments, the vasodilator is an admixture comprising carbon dioxide ($CO_2$). In some embodiments, the admixture comprising carbon dioxide ($CO_2$) further comprises oxygen ($O_2$). In some embodiments, the admixture comprising carbon dioxide ($CO_2$) is carbogen. "Carbogen" as used herein is an admixture of carbon dioxide and oxygen. The amounts of carbon dioxide and oxygen in the admixture may be determined by one of skill in the art. Medical grade carbogen is typically 5% $CO_2$ and 95% O2. In various embodiments, carbon dioxide is used to induce hyperemia may be an admixture of ranges including but not limited to 94% O2 and 6% $CO_2$, 93% O2 and 7% $CO_2$, 92% O2 and 8% $CO_2$, 91% O2 and 9% $CO_2$, 90% O2 and 10%

$CO_2$, 85% O2 and 15% $CO_2$, 80% O2 and 20% $CO_2$, 75% O2 and 25% $CO_2$, and/or 70% O2 and 30% $CO_2$.

In some embodiments, the admixture comprises any one or more of carbon dioxide, oxygen and nitrogen; carbon dioxide and oxygen; carbon dioxide and nitrogen, or carbon dioxide alone. In one embodiment, the amounts of $CO_2$ and $O_2$ administered are both altered. In some embodiments, the amount of $CO_2$ administered is altered to a predetermined level while the amount of $O_2$ administered is held constant. In some embodiments, the amounts of any one or more of $CO_2$, $O_2$ or $N_2$ in an admixture are changed or held constant as would be readily apparent to a person having ordinary skill in the art.

In some embodiments, the admixture comprising $CO_2$ is administered at high doses for short duration or at low doses for longer durations. For example, administering the admixture comprising $CO_2$ at high doses of $CO_2$ for a short duration comprises administering any one or more of 40 mmHg to 45 mmHg, 45 mmHg to 50 mmHg, 50 mmHg to 55 mmHg, 55 mmHg $CO_2$ to 60 mmHg $CO_2$, 60 mmHg $CO_2$ to 65 mmHg $CO_2$, 65 mmHg $CO_2$ to 70 mmHg $CO_2$, 70 mmHg $CO_2$ to 75 mmHg $CO_2$, 75 mmHg $CO_2$ to 80 mmHg $CO_2$, 80 mmHg $CO_2$ to 85 mm Hg $CO_2$ or a combination thereof, for about 20 minutes, 15 minutes, 10 minutes, 9 minutes, 8 minutes, 7 minutes, 6 minutes, 5 minutes, 4 minutes, 3 minutes, 2 minutes, 1 minute or a combination thereof. In some embodiments, the predetermined levels of $CO_2$ are administered so that the arterial level of $CO_2$ reaches the $PaCO_2$ of any one or more of the above ranges.

For example, administering low doses of predetermined amounts of $CO_2$ for a longer duration comprises administering the predetermined amount of $CO_2$ at any one or more of about 30 mmHg $CO_2$ to about 35 mmHg $CO_2$, about 35 mmHg $CO_2$ to about 40 mmHg $CO_2$, about 40 mmHg $CO_2$ to about 45 mmHg $CO_2$ or a combination thereof for any one or more of about 20 to 24 hours, about 15 to 20 hours, about 10 to 15 hours, about 5 to 10 hours, about 4 to 5 hours, about 3 to 4 hours, about 2 to 3 hours, about to 2 hours, or a combination thereof, before inducing hyperemia. In some embodiments, the predetermined levels of $CO_2$ are administered so that the arterial level of $CO_2$ reaches the $PaCO_2$ of any one or more of the above ranges.

In some embodiments, $CO_2$ is administered in a stepwise manner. In some embodiments, administering carbon dioxide in a stepwise manner includes administering carbon dioxide in 5 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mm-g to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In some embodiments, the predetermined levels of $CO_2$ are administered so that the arterial level of $CO_2$ reaches the $PaCO_2$ of any one or more of the above ranges.

In some embodiments, administering carbon dioxide in a stepwise manner includes administering carbon dioxide in 10 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In some embodiments, the predetermined levels of $CO_2$ are administered so that the arterial level of $CO_2$ reaches the $PaCO_2$ of any one or more of the above ranges.

In some embodiments, administering carbon dioxide in a stepwise manner includes administering carbon dioxide in 20 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In some embodiments, the predetermined levels of $CO_2$ are administered so that the arterial level of $CO_2$ reaches the $PaCO_2$ of any one or more of the above ranges.

In some embodiments, administering carbon dioxide in a stepwise manner includes administering carbon dioxide in 30 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg CO$_2$, 40 mmHg to 60 mmHg CO$_2$ or 50 mmHg to 60 mmHg CO$_2$. In some embodiments, the predetermined levels of CO$_2$ are administered so that the arterial level of CO$_2$ reaches the PaCO$_2$ of any one or more of the above ranges.

In some embodiments, administering carbon dioxide in a stepwise manner includes administering carbon dioxide in 40 mmHg increments in the range of any one or more of 10 mmHg to 100 mmHg CO$_2$, 20 mmHg to 100 mmHg CO$_2$, 30 mmHg to 100 mmHg CO$_2$, 40 mmHg to 100 mmHg CO$_2$, 50 mmHg to 100 mmHg CO$_2$, 60 mmHg to 100 mmHg CO$_2$, 10 mmHg to 90 mmHg CO$_2$, 20 mmHg to 90 mmHg CO$_2$, 30 mmHg to 90 mmHg CO$_2$, 40 mmHg to 90 mmHg CO$_2$, 50 mmHg to 90 mmHg CO$_2$, 60 mmHg to 90 mmHg CO$_2$, 10 mmHg to 80 mmHg CO$_2$, 20 mmHg to 80 mmHg CO$_2$, 30 mmHg to 80 mmHg CO$_2$, 40 mmHg to 80 mmHg CO$_2$, 50 mmHg to 80 mmHg CO$_2$, 60 mmHg to 80 mmHg CO$_2$, 10 mmHg to 70 mmHg CO$_2$, 20 mmHg to 70 mmHg CO$_2$, 30 mmHg to 70 mmHg CO$_2$, 40 mmHg to 70 mmHg CO$_2$, 50 mm g to 70 mmHg CO$_2$, 60 mmHg to 70 mmHg CO$_2$, 10 mm g to 60 mmHg CO$_2$, 20 mmHg to 70 mmHg CO$_2$, 30 mmHg to 70 mmHg CO$_2$, 40 mmHg to 70 mmHg CO$_2$, 50 mmHg to 70 mmHg CO$_2$, 60 mmHg to 70 mmHg CO$_2$, 10 mmHg to 60 mmHg CO$_2$, 20 mmHg to 60 mmHg CO$_2$, 30 mmHg to 60 mmHg CO$_2$, 40 mmHg to 60 mmHg CO$_2$ or 50 mmHg to 60 mmHg CO$_2$. In some embodiments, the predetermined levels of CO$_2$ are administered so that the arterial level of CO$_2$ reaches the PaCO$_2$ of any one or more of the above ranges.

In some embodiments, administering carbon dioxide in a stepwise manner includes administering carbon dioxide in 50 mmHg increments in the range of any one or more of 10 mmHg to 100 mmHg CO$_2$, 20 mmHg to 100 mmHg CO$_2$, 30 mmHg to 100 mmHg CO$_2$, 40 mmHg to 100 mmHg CO$_2$, 50 mmHg to 100 mmHg CO$_2$, 60 mmHg to 100 mmHg CO$_2$, 10 mmHg to 90 mmHg CO$_2$, 20 mmHg to 90 mmHg CO$_2$, 30 mmHg to 90 mmHg CO$_2$, 40 mmHg to 90 mmHg CO$_2$, 50 mmHg to 90 mmHg CO$_2$, 60 mmHg to 90 mmHg CO$_2$, 10 mmHg to 80 mmHg CO$_2$, 20 mmHg to 80 mmHg CO$_2$, 30 mmHg to 80 mmHg CO$_2$, 40 mmHg to 80 mmHg CO$_2$, 50 mmHg to 80 mmHg CO$_2$, 60 mmHg to 80 mmHg CO$_2$, 10 mmHg to 70 mmHg CO$_2$, 20 mmHg to 70 mmHg CO$_2$, 30 mmHg to 70 mmHg CO$_2$, 40 mmHg to 70 mmHg CO$_2$, 50 mmHg to 70 mmHg CO$_2$, 60 mmHg to 70 mmHg CO$_2$, 10 mm g to 60 mmHg CO$_2$, 20 mmHg to 70 mmHg CO$_2$, 30 mmHg to 70 mmHg CO$_2$, 40 mmHg to 70 mmHg CO$_2$, 50 mmHg to 70 mmHg CO$_2$, 60 mmHg to 70 mmHg CO$_2$, 10 mmHg to 60 mmHg CO$_2$, 20 mmHg to 60 mmHg CO$_2$, 30 mmHg to 60 mmHg CO$_2$, 40 mmHg to 60 mmHg CO$_2$ or 50 mmHg to 60 mmHg CO$_2$. In some embodiments, the predetermined levels of CO$_2$ are administered so that the arterial level of CO$_2$ reaches the PaCO$_2$ of any one or more of the above ranges.

Other increments of carbon dioxide to be administered in a stepwise manner will a readily apparent to a person having ordinary skill in the art.

In some embodiments, predetermined amount of CO$_2$ is administered in a block-wise manner. Block-wise administration of carbon dioxide comprises administering carbon dioxide in alternating amounts over a period of time. In alternating amounts of CO$_2$ comprises alternating between any of 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg. In some embodiments the predetermined levels of CO$_2$ are administered so that the arterial level of CO$_2$ reaches the PaCO$_2$ of any one or more of the above ranges. Other amounts of carbon dioxide to be used in alternating amounts over a period of time will be readily apparent to a person having ordinary skill in the art Other increments of carbon dioxide to be administered in a block-wise manner will a readily apparent to a person having ordinary skill in the art. 10168 In some embodiments the CO$_2$ gas is administered via inhalation. CO$_2$ may be administered using, for example, RespirACT™ technology from Thornhill Research. In some embodiments, CO$_2$ is administered for 1-2 minutes, 2-4 minutes, 4-6 minutes, 6-8 minutes, 8-10 minutes, 10-12 minutes, 12-14 minutes, 14-16 minutes, 16-18 minutes and/or 18-20 minutes. In some embodiments, CO$_2$ is administered for 4-6 minutes.

In some embodiments the CO$_2$ admixture is administered via inhalation. The CO$_2$ admixture may be administered using, for example, RespirACT™ technology from Thornhill Research. In some embodiments, the CO$_2$ admixture is administered for 1-2 minutes, 2-4 minutes, 4-6 minutes, 6-8 minutes, 8-10 minutes, 10-12 minutes, 12-14 minutes, 14-16 minutes, 16-18 minutes and/or 18-20 minutes. In some embodiments, the CO$_2$ admixture is administered for 4-6 minutes.

In some embodiments CO$_2$ is administered for an amount of time it takes for the arterial PaCO$_2$ (partial pressure of carbon dioxide) to reach 50-60 mmHg from the standard levels of 30 mmHg during CO-enhanced imaging.

In some embodiments CO$_2$ admixture is administered for an amount of time it takes for the arterial PaCO$_2$ (partial pressure of carbon dioxide) to reach 50-60 mmHg from the standard levels of 30 mmHg during CO$_2$-enhanced imaging.

In some embodiments, carbon dioxide used to induce hyperemia is medical-grade carbogen which is an admixture of 95% O$_2$ and 5% CO$_2$. In some embodiments, carbon dioxide is used to induce hyperemia may be an admixture of ranges including but not limited to 94% O$_2$ and 6% CO$_2$, 93% O$_2$ and 7% CO$_2$, 92% O$_2$ and 8% CO$_2$, 91% O$_2$ and 9% CO$_2$, 90% O$_2$ and 10% CO$_2$, 85% O$_2$ and 15% CO$_2$, 80% O$_2$ and 20% CO$_2$, 75% O$_2$ and 25% CO$_2$ and/or 70% O$_2$ and 30% CO$_2$.

In some embodiments, the imaging techniques using carbon dioxide involve a free-breathing approach so as to permit entry CO$_2$ into the subject's system.

In some embodiments, the vasodilator is administered to the subject so as to reach a predetermined PaCO$_2$ in the subject.

In various embodiments, no radioactive tracer or contrast agent is administered to the subject. In various embodiments, imaging the subject's cardiovascular system comprises imaging the subject's heart. In various embodiments, imaging the subject's cardiovascular system comprises imaging the subject's coronary arteries. In various embodiments, imaging the subject's cardiovascular system comprises imaging the subject's myocardium.

In various embodiments, imaging the subject's myocardium comprises (i) obtaining free-breathing cardiac phase resolved 2D or 3D myocardial BOLD images; (ii) registering and segmenting the BOLD images to obtain the myocardial dynamic volume; and (iii) identifying ischemic territory and quantify image volume.

In various embodiments, imaging the subject's cardiovascular system and/or imaging at least a portion of the subject's cardiovascular system comprises one or more imaging modalities and/or imaging methods and/or imaging techniques. In various embodiments, imaging the subject's cardiovascular system and/or imaging at least a portion of the subject's cardiovascular system comprises performing one or more imaging modalities and/or imaging methods and/or imaging techniques. In various embodiments, imaging the subject's cardiovascular system and/or imaging at least a portion of the subject's cardiovascular system comprises using one or more imaging modalities and/or imaging methods and/or imaging techniques. Examples of suitable imaging modalities and/or imaging methods and/or imaging techniques include but are not limited to using positron emission tomography (PET), single photon emission computed tomography (SPECT), computed tomography (CT), magnetic resonance imaging (MRI), blood-contrast-based magnetic resonance imaging (including perfusion sensitive magnetic resonance imaging, blood oxygenation sensitive magnetic resonance imaging, blood flow sensitive magnetic resonance imaging, blood volume sensitive magnetic resonance imaging, blood-oxygen-level dependent magnetic resonance imaging (BOLD MRI), and combinations thereof), electron-beam computed tomography (EBCT), electron spin resonance (ESR), positron emission tomography/computed tomography (PET/CT), single photon emission computed tomography/computed tomography (SPECT/CT), positron emission tomography/magnetic resonance (PET/MR), positron emission tomography/magnetic resonance imaging (PET/MRI), and single photon emission computed tomography/magnetic resonance (SPECT/MR), single photon emission computed tomography/magnetic resonance imaging (SPECT/MRI), and their various combinations. In some embodiments, blood-contrast-based magnetic resonance imaging is used for imaging the subject's cardiovascular system and/or imaging at least a portion of the subject's cardiovascular system. In some embodiments, blood-contrast-based magnetic resonance imaging is selected from the group consisting of perfusion sensitive magnetic resonance imaging, blood oxygenation sensitive magnetic resonance imaging, blood flow sensitive magnetic resonance imaging, blood volume sensitive magnetic resonance imaging, blood-oxygen-level dependent magnetic resonance imaging (BOLD MRI), and combinations thereof. In some embodiments, blood-oxygen-level dependent magnetic resonance imaging (BOLD MRI) is used for imaging the subject's cardiovascular system and/or imaging at least a portion of the subject's cardiovascular system.

In some embodiments, imaging the subject's cardiovascular system and/or imaging at least a portion of the subject's cardiovascular system comprises operating imaging equipment. In some embodiments, the imaging equipment is medical imaging equipment. In some embodiments, the imaging equipment is diagnostic imaging equipment. In some embodiments, the imaging equipment is selected from the group consisting of computed tomography (CT) scanner, positron emission tomography (PET) scanner, computed tomography (CT)/positron emission tomography (PET) scanner, magnetic resonance imaging (MRI) scanner, nuclear medicine camera (e.g., a gamma camera), x-ray machine and equipment, ultrasound machine and equipment, electron-beam computed tomography (EBCT) scanner, single photon emission computed tomography (SPECT) scanner, positron emission tomography/magnetic resonance imaging (PET/MRI) scanner, single photon emission computed tomography/magnetic resonance imaging (SPECT/MRI) scanner, and combinations thereof. In some embodiments, the imaging equipment is a magnetic resonance imaging (MRI) scanner.

In some embodiments, imaging the at least a portion of the subject's cardiovascular system at rest comprises operating imaging equipment and performing an imaging technique. In some embodiments, imaging of the at least a portion of the subject's cardiovascular system at stress comprises operating imaging equipment and performing an imaging technique. In some embodiments, imaging of the at least a portion of the subject's cardiovascular system after administration of the stress agent comprises operating imaging equipment and performing an imaging technique.

In various embodiments, imaging the subject's cardiovascular system comprises blood-oxygen-level dependent (BOLD) magnetic resonance imaging (MRI) of the subject's cardiovascular system. In various embodiments, imaging the subject's cardiovascular system comprises performing myocardial perfusion imaging (MPI). In various embodiments, MPI is performed using blood-oxygen-level dependent (BOLD) magnetic resonance imaging (MRI). In some embodiments, the method further comprises calculating and/or measuring and/or determining myocardial BOLD response.

In various embodiments, imaging at least a portion of the subject's cardiovascular system comprises blood-oxygen-level dependent (BOLD) magnetic resonance imaging (MRI) of the at least a portion of the subject's cardiovascular system. In various embodiments, imaging at least a portion of the subject's cardiovascular system comprises performing myocardial perfusion imaging (MPI) of the at least a portion of the subject's cardiovascular system. In various embodiments, MPI is performed using blood-oxygen-level dependent (BOLD) magnetic resonance imaging (MRI). In some embodiments, the method further comprises calculating and/or measuring and/or determining myocardial BOLD response.

In some embodiments, the blood oxygen level dependent magnetic resonance imaging (BOLD-MRI) is not ECG-gated. In some embodiments, the blood oxygen level dependent magnetic resonance imaging (BOLD-MRI) is free-breathing. In some embodiments, the blood oxygen level dependent magnetic resonance imaging (BOLD-MRI) is respiratory and cardiac phase-resolved. In some embodiments, the blood oxygen level dependent magnetic resonance imaging (BOLD-MRI) comprises a T2-based sequence at 3T, wherein the T2-based sequence at 3T comprises a low rank tensor (LRT).

In various embodiments, time-dependent T2 maps were used to model the vascular relaxation as $T_2(t)=T_{2o}+\Delta_{T2max} \exp(-t/\tau)$, where $T_{2o}=T_2$ at rest; $\Delta T_{2max}$=maximal $T_2$ change from rest; t=time; and $\tau$=time constant of vascular relaxation.

In some embodiments, the vascular relaxation is indexed as a time constant. In some embodiments, the time constant of vascular relaxation is a measure of extent of the cardiovascular disease in the subject.

In various embodiments, the upraising part of the curve will be fitted with $T_2(t)=T_{2o}+(T_{2i}-T_{2o})(\exp(-t/\tau_a)-\exp(-t/\sigma_d))$, where $T_{2o}=T_2$ at rest; $T_{2i}$=the $T_2$ intercept with the time plot; t=time; $\tau_a$=the time constant of the raising part; and $\tau_d$=time constant of vascular relaxation during the decaying period.

In some embodiments, the vascular reactivity is indexed as a time constant of the raising part. In some embodiments, the vascular reactivity is indexed as a time constant of the raising part of the curve. In some embodiments, the vascular reactivity is indexed as a time constant of the raising part of a BOLD response. In some embodiments, the vascular reactivity is indexed as a time constant in a rising part of a BOLD response. In some embodiments, the time constant of the raising part is a measure of extent of the cardiovascular disease in the subject. In some embodiments, the time constant in a rising part is a measure of extent of the cardiovascular disease in the subject. In some embodiments, the time constant in a rising part is the same as the time constant of the raising part.

In some embodiments, the vascular relaxation is indexed as a time constant of vascular relaxation during the decaying period. In some embodiments, the vascular relaxation is indexed as a time constant of vascular relaxation during the decaying period of the curve. In some embodiments, the vascular relaxation is indexed as a time constant of vascular relaxation during the decaying period of a BOLD response. In some embodiments, the vascular relaxation is indexed as a time constant in a falling part of the BOLD response. In some embodiments, the time constant of vascular relaxation during the decaying period is a measure of extent of the cardiovascular disease in the subject. In some embodiments, the time constant of vascular relaxation during a falling part is a measure of extent of the cardiovascular disease in the subject. In some embodiments, the time constant during the decaying period is the same as the time constant in a falling part.

In some embodiments, a method described herein may be performed at the prevention stage of a symptom, disease, disorder, or disease condition (i.e., when the subject has not developed the symptom, disease, disorder, or disease condition but is likely to or in the process of developing the symptom, disease, disorder, or disease condition). In other embodiments, a method described herein may be performed at the treatment stage of a symptom, disease, disorder, or disease condition (i.e., when the subject has already developed the symptom, disease, disorder, or disease condition).

In some embodiments, the BOLD MRI used for imaging the subject's cardiovascular system is non-contrast $T_2$, $T_2^*$, or $T_1$ mapping (for example at 1.5T or 3T), which does not require exogenous contrast media. Therefore, the technique can be safely used even in patients for whom Late Gadolinium Enhancement (LGE) imaging and contrast-enhanced $T_1$ mapping are contraindicated. In various embodiments, the BOLD MRI used for imaging the subject's cardiovascular system is any one or more of non-contrast $T_1$-mapping, $T_1$-weighted imaging, inversion-recovery prepared $T_1$-weighted imaging, $T_2$-weighted images, $T_2$ maps, $T_2^*$-weighted images, $T_2^*$ maps, diffusion-weighted images, apparent-diffusion-coefficient (ADC) maps, steady-state free precession CINE images, steady-state free precession non-CINE images, steady-state free precession coherent images, incoherent steady-state free precession images, myocardial tags, magnetization transfer (MT) weighted and MT rate (MTR) images, or a combination thereof, which does not require exogenous contrast media.

In various embodiments, a method described herein may be performed once, twice, three or more times. In various embodiments, a method described herein may be performed 1-3 times per day, 1-7 times per week, 1-9 times per month, or 1-12 times per year. In various embodiments, a method described herein may be performed for about 1-6 hours, 7-12 hours, 13-18 hours, 19-24 hours, 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

In some embodiments, a non-contrast approach is used for imaging the subject's cardiovascular system, wherein the non-contrast approach includes but is not limited to blood oxygen level dependent (BOLD) magnetic resonance imaging (MRI). In some embodiments, a non-contrast approach is used for imaging the subject's cardiovascular system, wherein the non-contrast approach is blood oxygen level dependent (BOLD) magnetic resonance imaging (MRI).

In some embodiments, a non-contrast approach is used for imaging at least a portion of the subject's cardiovascular system, wherein the non-contrast approach includes but is not limited to blood oxygen level dependent (BOLD) magnetic resonance imaging (MRI). In some embodiments, a non-contrast approach is used for imaging at least a portion of the subject's cardiovascular system, wherein the non-contrast approach is blood oxygen level dependent (BOLD) magnetic resonance imaging (MRI).

In various embodiments, the time interval between each stress image obtained during imaging comprises a beat-to-beat heartbeat interval. In various embodiments, the time interval between each stress image obtained during imaging is a beat-to-beat heartbeat interval. In various embodiments, the time interval between each stress image obtained during imaging is less than a beat-to-beat heartbeat interval.

In various embodiments, the time interval between each rest image obtained during imaging comprises a beat-to-beat heartbeat interval. In various embodiments, the time interval between each rest image obtained during imaging is a beat-to-beat heartbeat interval. In various embodiments, the time interval between each rest image obtained during imaging is less than a beat-to-beat heartbeat interval.

In various embodiments, the time interval between each stress image obtained during imaging comprises a heartbeat interval. In various embodiments, the time interval between each stress image obtained during imaging is a heartbeat interval. In various embodiments, the time interval between each stress image obtained during imaging is less than a heartbeat interval.

In various embodiments, the time interval between each rest image obtained during imaging comprises a heartbeat interval. In various embodiments, the time interval between each rest image obtained during imaging is a heartbeat interval. In various embodiments, the time interval between each rest image obtained during imaging is less than a heartbeat interval.

In various embodiments, the time interval between each stress image obtained during imaging comprises a time interval between two heartbeats. In various embodiments, the time interval between each stress image obtained during imaging is a time interval between two heartbeats. In various embodiments, the time interval between each stress image obtained during imaging is less than a time interval between two heartbeats.

In various embodiments, the time interval between each rest image obtained during imaging comprises a time interval between two heartbeats. In various embodiments, the time interval between each rest image obtained during imaging is a time interval between two heartbeats. In various embodiments, the time interval between each rest image obtained during imaging is less than a time interval between two heartbeats.

Without being bound by theory, a heart rhythm will have some variation, even in a healthy, normal person. For a normal, healthy person, the variance is typically limited. So for example, general population studies have indicated that the typical variance in time between heartbeats for a healthy, normal heart is less than 125 milliseconds beat-to-beat.

In various embodiments, an effective amount of a vasodilator is administered to the subject, wherein the vasodilator has an extended vasodilatory state. Examples of an extended vasodilatory state include but are not limited to a terminal half-life of 33-108 min for regadenoson (Al Jaroudi W, Iskandrian A E. Regadenoson: a new myocardial stress agent. Journal of the American College of Cardiology 2009; 54:1123-30), 10-120 min for binodenoson, 5 min for apadenoson, and 40 min to 10 hours for dipyridamole (Zoghbi G J, Iskandrian A E. Selective adenosine agonists and myocardial perfusion imaging. J. Nucl. Cardiol. 2012 19:1,126-141).

In various embodiments, the vasodilator may be provided as pharmaceutical compositions. In various embodiments, the pharmaceutical compositions according to the invention may be formulated for delivery via any route of administration. "Route of administration" may refer to any administration pathway known in the art, including but not limited to aerosol, nasal, via inhalation, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art. In certain embodiments, the pharmaceutical compositions are formulated for intravascular, intravenous, or intraarterial administration. In one embodiment, the pharmaceutical compositions are formulated for intravenous administration as a single bolus.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body.

In some embodiments, wherein the reference is a control subject, wherein the control subject does not have the cardiovascular disease. In some embodiments, the reference is the subject at an earlier point in time. In some embodiments, the reference is another subject that has been treated for the cardiovascular disease.

In some embodiments, the change in the response to oxygenation and blood flow is a decrease in the response to oxygenation and blood flow in the at least a portion of the subject's cardiovascular system compared to the at least a portion of the cardiovascular system in the reference. In some embodiments, the decrease in the response is in an affected territory of the at least a portion of the subject's cardiovascular system.

In some embodiments, the change is an increase in the vascular reactivity in the at least a portion of the subject's cardiovascular system compared to the vascular reactivity in the at least a portion of a cardiovascular system from the reference.

In some embodiments, the change is a decrease in the vascular reactivity in the at least a portion of the subject's cardiovascular system compared to the vascular reactivity in the at least a portion of a cardiovascular system from the reference.

In some embodiments, any of the methods of the present invention further comprise detecting in the subject at least one selected from the group consisting of a hyperemia response, myocardial perfusion reserve, perfusion, myocardial perfusion, and combinations thereof.

Many variations and alternative elements have been disclosed in embodiments of the present invention. Still further variations and alternate elements will be apparent to one of skill in the art. Among these variations, without limitation, is the selection of steps, pharmaceutical compositions, administration routes and devices, imaging equipment, imaging technologies for the inventive methods, and the diseases and other disease conditions that may be diagnosed, prognosed or treated therewith. Various embodiments of the invention can specifically include or exclude any of these variations or elements.

Some embodiments of the present invention can be defined as any of the following numbered paragraphs:

1. A method for identifying and/or assessing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess a response to at least one of oxygenation and blood flow in the cardiovascular system, wherein a change in the response relative to a reference sample is indicative of cardiovascular disease in the subject.

2. A method for detecting cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess a response to at least one of oxygenation and blood flow in the cardiovascular system, wherein a change in the response relative to a reference sample is indicative of cardiovascular disease in the subject.

3. A method for prognosing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess a response to at least one of oxygenation and blood flow in the cardiovascular system, wherein a change in the response relative to a reference sample is a prognosis of cardiovascular disease in the subject.

4. A method for determining progression of cardiovascular disease in a subject, comprising:
(a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess a response to at least one of oxygenation and blood flow in the cardiovascular system, wherein a change in the response relative to a reference sample is indicative of progression of cardiovascular disease in the subject.

5. A method for diagnosing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess a response to at least one of oxygenation and blood flow in the cardiovascular system, wherein a change in the response relative to a reference sample is a diagnosis of cardiovascular disease in the subject.

6. A method for assessing and/or determining the risk of developing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess a response to at least one of oxygenation and blood flow in the cardiovascular system, wherein a change in the response relative to a reference sample is indicative of an increased risk of the subject developing cardiovascular disease.

7. The method of any one of paragraphs 1, 2, 3, 4, 5, or 6, wherein the change is a decrease in the response relative to a reference sample.

8. The method of paragraph 7, wherein the decrease in the response is in an affected territory of the cardiovascular system of the subject.

9. The method of any one of paragraphs 1, 2, 3, 4, 5, or 6, wherein the blood oxygen level dependent magnetic resonance imaging (BOLD-MRI) is not ECG-gated.

10. The method of any one of paragraphs 1, 2, 3, 4, 5, or 6, wherein the blood oxygen level dependent magnetic resonance imaging (BOLD-MRI) is free-breathing.

11. The method of any one of paragraphs 1, 2, 3, 4, 5, or 6, wherein the blood oxygen level dependent magnetic resonance imaging (BOLD-MRI) is respiratory and cardiac phase-resolved.

12. The method of any one of paragraphs 1, 2, 3, 4, 5, or 6, wherein the blood oxygen level dependent magnetic resonance imaging (BOLD-MRI) comprises a T2-based sequence at 3T, wherein the T2-based sequence at 3T comprises a low rank tensor (LRT).

13. The method of any one of paragraphs 1, 2, 3, 4, 5, or 6, wherein the cardiovascular system comprises a heart.

14. The method of any one of paragraphs 1, 2, 3, 4, 5, or 6, wherein the cardiovascular system comprises a myocardium.

15. The method of any one of paragraphs 1, 2, 3, 4, 5, or 6, wherein the cardiovascular system comprises at least one coronary artery.

16. The method of any one of paragraphs 1, 2, 3, 4, 5, or 6, wherein the vasodilator is selected from the group consisting of regadenoson, binodenoson, apadenoson, dipyridamole, adenosine, and combinations thereof.

17. The method of any one of paragraphs 1, 2, 3, 4, 5, or 6, wherein the vasodilator is regadenoson.

18. The method of any one of paragraphs 1, 2, 3, 4, 5, or 6, wherein the vasodilator induces hyperemia.

19. The method of any one of paragraphs 1, 2, 3, 4, 5, or 6, wherein the vasodilator is a selective A2A adenosine receptor agonist.

20. The method of paragraph 19, wherein the selective A2A adenosine receptor agonist is regadenoson, or a functional equivalent, analog, derivative or salt.

21. The method of any one of paragraphs 1, 2, 3, 4, 5, or 6, wherein the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof.

22. The method of any one of paragraphs 1, 2, 3, 4, 5, or 6, wherein the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

23. The method of any one of paragraphs 1, 2, 3, 4, 5, or 6, wherein the vasodilator is administered intravascularly, intravenously, intraarterially, or intracoronary.

24. The method of any one of paragraphs 1, 2, 3, 4, 5, or 6, wherein the vasodilator is administered as a single bolus.

25. The method of paragraph 24, wherein the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

26. The method of any one of paragraphs 1, 2, 3, 4, 5, or 6, wherein the vasodilator comprises $CO_2$.

27. The method of any one of paragraphs 1, 2, 3, 4, 5, or 6, wherein the vasodilator is selected from the group consisting of $CO_2$, and an admixture comprising $CO_2$.

28. The method of any one of paragraphs 26 or 27, wherein the vasodilator is administered by inhalation.

29. The method of any one of paragraphs 26 or 27, wherein the vasodilator is administered in a stepwise manner.

30. The method of any one of paragraphs 26 or 27, wherein the vasodilator is administered to the subject so as to reach a predetermined $PaCO_2$ in the subject.

31. The method of any one of paragraphs 1, 2, 3, 4, 5, or 6, wherein the period of time is selected from a group consisting of at least 1 hour, at least 30 minutes, at least 15 minutes, at least 10 minutes, at least 5 minutes, and at least 1 minute.

32. The method of any one of paragraphs 1, 2, 3, 4, 5, or 6, wherein the period of time is selected from a group consisting of up to 2 hours, up to 1 hour, up to 30 minutes, up to 15 minutes, and up to 10 minutes.

33. The method of any one of paragraphs 1, 2, 3, 4, 5, or 6, wherein step (c) is performed about 0.1-0.5, 0.5-1, 1-5, 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b).

34. The method of any one of paragraphs 1, 2, 3, 4, 5, or 6, wherein no radioactive tracer or contrast agent is administered to the subject.

35. The method of any one of paragraphs 1, 2, 3, 4, 5, or 6, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease.

36. The method of any one or paragraphs 1, 2, 3, 4, 5, or 6, wherein the cardiovascular disease is ischemic heart disease.

37. The method of any one or paragraphs 1, 2, 3, 4, 5, or 6, wherein the cardiovascular disease is infarcted myocardium.

38. The method of any one or paragraphs 1, 2, 3, 4, 5, or 6, wherein the reference sample is obtained from a control subject, wherein the control subject does not have the cardiovascular disease.

39. The method of any one or paragraphs 1, 2, 3, 4, 5, or 6, wherein the reference sample is obtained from the subject before the subject is treated for the cardiovascular disease.

40. The method of any one or paragraphs 1, 2, 3, 4, 5, or 6, wherein the reference sample is from a subject that has been successfully treated for the cardiovascular disease.

41. The method of any one or paragraphs 1, 2, 3, 4, 5, or 6, further comprising treating the subject and/or selecting a treatment for the subject and/or providing a treatment to the subject and/or administering a treatment to the subject.

42. The method of any one or paragraphs 1, 2, 3, 4, 5, or 6, further comprising selecting a preventative treatment for the subject and/or providing a preventative treatment to the subject and/or administering a preventative treatment to the subject.

43. A method for identifying and/or assessing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to at least one image from a reference sample, wherein a change in the motion corrected images relative to the at least one image from the reference sample is indicative of cardiovascular disease in the subject.

44. A method for detecting cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to at least one image from a reference sample, wherein a change in the motion corrected images relative to the at least one image from the reference sample is indicative of cardiovascular disease in the subject.

45. A method for prognosing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to at least one image from a reference sample, wherein a change in the motion corrected images relative to the at least one image from the reference sample is a prognosis of cardiovascular disease in the subject.

46. A method for determining progression of cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to at least one image from a reference sample, wherein a change in the motion corrected images relative to the at least one image from the reference sample is indicative of progression of cardiovascular disease in the subject.

47. A method for diagnosing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to at least one image from a reference sample, wherein a change in the motion corrected images relative to the at least one image from the reference sample is a diagnosis of cardiovascular disease in the subject.

48. A method for assessing and/or determining the risk of developing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to at least one image from a reference sample, wherein a change in the motion corrected images relative to the at least one image from the reference sample is indicative of an increased risk of the subject developing cardiovascular disease.

49. The method of any one of paragraphs 43, 44, 45, 46, 47, or 48, wherein the change is in an affected territory of the cardiovascular system of the subject.

50. The method of any one of paragraphs 43, 44, 45, 46, 47, or 48, wherein the blood oxygen level dependent magnetic resonance imaging (BOLD-MRI) is not ECG-gated.

51. The method of any one of paragraphs 43, 44, 45, 46, 47, or 48, wherein the blood oxygen level dependent magnetic resonance imaging (BOLD-MRI) is free-breathing.

52. The method of any one of paragraphs 43, 44, 45, 46, 47, or 48, wherein the blood oxygen level dependent magnetic resonance imaging (BOLD-MRI) is respiratory and cardiac phase-resolved.

53. The method of any one of paragraphs 43, 44, 45, 46, 47, or 48, wherein the blood oxygen level dependent magnetic resonance imaging (BOLD-MRI) comprises a T2-based sequence at 3T, wherein the T2-based sequence at 3T comprises a low rank tensor (LRT).

54. The method of any one of paragraphs 43, 44, 45, 46, 47, or 48, wherein the cardiovascular system comprises a heart.

55. The method of any one of paragraphs 43, 44, 45, 46, 47, or 48, wherein the cardiovascular system comprises a myocardium.

56. The method of any one of paragraphs 43, 44, 45, 46, 47, or 48, wherein the cardiovascular system comprises at least one coronary artery.

57. The method of any one of paragraphs 43, 44, 45, 46, 47, or 48, wherein the vasodilator is selected from the group consisting of regadenoson, binodenoson, apadenoson, dipyridamole, adenosine, and combinations thereof.

58. The method of any one of paragraphs 43, 44, 45, 46, 47, or 48, wherein the vasodilator is regadenoson.

59. The method of any one of paragraphs 43, 44, 45, 46, 47, or 48, wherein the vasodilator induces hyperemia.

60. The method of any one of paragraphs 43, 44, 45, 46, 47, or 48, wherein the vasodilator is a selective A2A adenosine receptor agonist.

61. The method of paragraph 60, wherein the selective A2A adenosine receptor agonist is regadenoson, or a functional equivalent, analog, derivative or salt.

62. The method of any one of paragraphs 43, 44, 45, 46, 47, or 48, wherein the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof.

63. The method of any one of paragraphs 43, 44, 45, 46, 47, or 48, wherein the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

64. The method of any one of paragraphs 43, 44, 45, 46, 47, or 48, wherein the vasodilator is administered intravascularly, intravenously, intraarterially, or intracoronary.

65. The method of any one of paragraphs 43, 44, 45, 46, 47, or 48, wherein the vasodilator is administered as a single bolus.

66. The method of paragraph 65, wherein the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

67. The method of any one of paragraphs 43, 44, 45, 46, 47, or 48, wherein the vasodilator comprises $CO_2$.

68. The method of any one of paragraphs 43, 44, 45, 46, 47, or 48, wherein the vasodilator is selected from the group consisting of $CO_2$, and an admixture comprising $CO_2$.

69. The method of any one of paragraph 67 or 68, wherein the vasodilator is administered by inhalation.

70. The method of any one of paragraph 67 or 68, wherein the vasodilator is administered in a stepwise manner.

71. The method of any one of paragraph 67 or 68, wherein the vasodilator is administered to the subject so as to reach a predetermined $PaCO_2$ in the subject.

72. The method of any one of paragraphs 43, 44, 45, 46, 47, or 48, wherein the period of time is selected from a group consisting of at least 1 hour, at least 30 minutes, at least 15 minutes, at least 10 minutes, at least 5 minutes, and at least 1 minute.

73. The method of any one of paragraphs 43, 44, 45, 46, 47, or 48, wherein the period of time is selected from a group consisting of up to 2 hours, up to 1 hour, up to 30 minutes, up to 15 minutes, and up to 10 minutes.

74. The method of any one of paragraphs 43, 44, 45, 46, 47, or 48, wherein step (c) is performed about 0.1-0.5, 0.5-1, 1-5, 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b).

75. The method of any one of paragraphs 43, 44, 45, 46, 47, or 48, wherein no radioactive tracer or contrast agent is administered to the subject.

76. The method of any one of paragraphs 43, 44, 45, 46, 47, or 48, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease.

77. The method of any one of paragraphs 43, 44, 45, 46, 47, or 48, wherein the cardiovascular disease is ischemic heart disease.

78. The method of any one of paragraphs 43, 44, 45, 46, 47, or 48, wherein the cardiovascular disease is infarcted myocardium.

79. The method of any one of paragraphs 43, 44, 45, 46, 47, or 48, wherein the reference sample is obtained from a control subject, wherein the control subject does not have the cardiovascular disease.

80. The method of any one of paragraphs 43, 44, 45, 46, 47, or 48, wherein the reference sample is obtained from the subject before the subject is treated for the cardiovascular disease.

81. The method of any one of paragraphs 43, 44, 45, 46, 47, or 48, wherein the reference sample is from a subject that has been successfully treated for the cardiovascular disease.

82. A method for identifying and/or assessing cardiovascular disease in a subject, comprising: (a) imaging a cardiovascular system in the subject at rest to obtain a rest image and rest data; (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess at least one of vascular reactivity in the cardiovascular system of the subject, wherein a change in the vascular reactivity relative to a reference sample is indicative of cardiovascular disease in the subject.

83. A method for detecting cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess at least one of vascular reactivity in the cardiovascular system of the subject, wherein a change in the vascular reactivity relative to a reference sample is indicative of cardiovascular disease in the subject.

84. A method for prognosing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess at least one of vascular reactivity in the cardiovascular system of the subject, wherein a change in the vascular reactivity relative to a reference sample is a prognosis of cardiovascular disease in the subject.

85. A method for determining progression of cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess at least one of vascular reactivity in the cardiovascular system of the subject, wherein a change in the vascular reactivity relative to a reference sample is indicative of progression of cardiovascular disease in the subject.

86. A method for diagnosing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess at least one of vascular reactivity in the cardiovascular system of the subject, wherein a change in the vascular reactivity relative to a reference sample is a diagnosis of cardiovascular disease in the subject.

87. A method for assessing and/or determining the risk of developing cardiovascular disease in a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; (d) registering the stress images to the rest image to obtain a plurality of motion-corrected images; and (e) comparing the plurality of motion corrected images to assess at least one of vascular reactivity in the cardiovascular system of the subject, wherein a change in the vascular reactivity relative to a reference sample is indicative of an increased risk of the subject developing cardiovascular disease.

88. The method of any one of paragraphs 82, 83, 84, 85, 86, or 87, wherein the change is in an affected territory of the cardiovascular system of the subject.

89. The method of any one of paragraphs 82, 83, 84, 85, 86, or 87, wherein the change is a decrease in the vascular reactivity relative to a reference sample.

90. The method of any one of paragraphs 82, 83, 84, 85, 86, or 87, wherein the change is an increase in the vascular reactivity relative to a reference sample.

91. The method of any one of paragraphs 82, 83, 84, 85, 86, or 87, further comprising calculating and/or measuring and/or determining and/or monitoring and/or detecting and/or assessing at least one selected from the group consisting of a hyperemia response, myocardial perfusion reserve, perfusion, myocardial perfusion, and combinations thereof.

92. The method of any one of paragraphs 82, 83, 84, 85, 86, or 87, wherein the blood oxygen level dependent magnetic resonance imaging (BOLD-MRI) is not ECG-gated.

93. The method of any one of paragraphs 82, 83, 84, 85, 86, or 87, wherein the blood oxygen level dependent magnetic resonance imaging (BOLD-MRI) is free-breathing.

94. The method of any one of paragraphs 82, 83, 84, 85, 86, or 87, wherein the blood oxygen level dependent magnetic resonance imaging (BOLD-MRI) is respiratory and cardiac phase-resolved.

95. The method of any one of paragraphs 82, 83, 84, 85, 86, or 87, wherein the blood oxygen level dependent magnetic resonance imaging (BOLD-MRI) comprises a T2-based sequence at 3T, wherein the T2-based sequence at 3T comprises a low rank tensor (LRT).

96. The method of any one of paragraphs 82, 83, 84, 85, 86, or 87, wherein the cardiovascular system comprises a heart.

97. The method of any one of paragraphs 82, 83, 84, 85, 86, or 87, wherein the cardiovascular system comprises a myocardium.

98. The method of any one of paragraphs 82, 83, 84, 85, 86, or 87, wherein the cardiovascular system comprises at least one coronary artery.

99. The method of any one of paragraphs 82, 83, 84, 85, 86, or 87, wherein the vasodilator is selected from the group consisting of regadenoson, binodenoson, apadenoson, dipyridamole, adenosine, and combinations thereof.

100. The method of any one of paragraphs 82, 83, 84, 85, 86, or 87, wherein the vasodilator is regadenoson.

101. The method of any one of paragraphs 82, 83, 84, 85, 86, or 87, wherein the vasodilator induces hyperemia.

102. The method of any one of paragraphs 82, 83, 84, 85, 86, or 87, wherein the vasodilator is a selective A2A adenosine receptor agonist.

103. The method of paragraph 102, wherein the selective A2A adenosine receptor agonist is regadenoson, or a functional equivalent, analog, derivative or salt.

104. The method of any one of paragraphs 82, 83, 84, 85, 86, or 87, wherein the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof.

105. The method of any one of paragraphs 82, 83, 84, 85, 86, or 87, wherein the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

106. The method of any one of paragraphs 82, 83, 84, 85, 86, or 87, wherein the vasodilator is administered intravascularly, intravenously, intraarterially, or intracoronary.

107. The method of any one of paragraphs 82, 83, 84, 85, 86, or 87, wherein the vasodilator is administered as a single bolus.

108. The method of paragraph 107, wherein the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

109. The method of any one of paragraphs 82, 83, 84, 85, 86, or 87, wherein the vasodilator comprises $CO_2$.

110. The method of any one of paragraphs 82, 83, 84, 85, 86, or 87, wherein the vasodilator is selected from the group consisting of $CO_2$, and an admixture comprising $CO_2$.

111. The method of any one of paragraphs 109 or 110, wherein the vasodilator is administered by inhalation.

112. The method of any one of paragraphs 109 or 110, wherein the vasodilator is administered in a stepwise manner.

113. The method of any one of paragraphs 109 or 110, wherein the vasodilator is administered to the subject so as to reach a predetermined $PaCO_2$ in the subject.

114. The method of any one of paragraphs 82, 83, 84, 85, 86, or 87, wherein the period of time is selected from a group consisting of at least 1 hour, at least 30 minutes, at least 15 minutes, at least 10 minutes, at least 5 minutes, and at least 1 minute.

115. The method of anyone of paragraphs 82, 83, 84, 85, 86, or 87, wherein the period of time is selected from a group consisting of up to 2 hours, up to 1 hour, up to 30 minutes, up to 15 minutes, and up to 10 minutes.

116. The method of any one of paragraphs 82, 83, 84, 85, 86, or 87, wherein step (c) is performed about 0.1-0.5, 0.5-1, 1-5, 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b).

117. The method of any one of paragraphs 82, 83, 84, 85, 86, or 87, wherein no radioactive tracer or contrast agent is administered to the subject.

118. The method of any one of paragraphs 82, 83, 84, 85, 86, or 87, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease.

119. The method of any one of paragraphs 82, 83, 84, 85, 86, or 87, wherein the cardiovascular disease is ischemic heart disease.

120. The method of any one of paragraphs 82, 83, 84, 85, 86, or 87, wherein the cardiovascular disease is infarcted myocardium.

121. The method of any one of paragraphs 82, 83, 84, 85, 86, or 87, wherein the reference sample is obtained from a control subject, wherein the control subject does not have the cardiovascular disease.

122. The method of any one of paragraphs 82, 83, 84, 85, 86, or 87, wherein the reference sample is obtained from the subject before the subject is treated for the cardiovascular disease.

123. The method of any one of paragraphs 82, 83, 84, 85, 86, or 87, wherein the reference sample is from a subject that has been successfully treated for the cardiovascular disease.

124. A method for imaging a cardiovascular system of a subject, comprising: (a) imaging a cardiovascular system in the subject at rest to obtain a rest image and rest data, wherein the imaging is performed by blood oxygen level dependent magnetic resonance imaging (BOLD-MRI); (b) administering an effective amount of at least one stress agent to the subject, wherein the stress agent is at least one vasodilator; (c) imaging the cardiovascular system in the subject after administration of the stress agent over a period of time to obtain a series of stress images and stress data, wherein the imaging is performed by blood oxygen level dependent magnetic resonance imaging (BOLD-MRI), wherein the stress images and stress data are obtained at a time interval between each stress image, wherein the time interval between each stress image is a beat-to-beat heartbeat interval; and (d) registering the stress images to the rest image to obtain a plurality of motion-corrected images of the cardiovascular system of the subject.

125. The method of paragraph 124, wherein the blood oxygen level dependent magnetic resonance imaging (BOLD-MRI) is not ECG-gated.

126. The method of paragraph 124, wherein the blood oxygen level dependent magnetic resonance imaging (BOLD-MRI) is free-breathing.

127. The method of paragraph 124, wherein the blood oxygen level dependent magnetic resonance imaging (BOLD-MRI) is respiratory and cardiac phase-resolved.

128. The method of paragraph 124, wherein the blood oxygen level dependent magnetic resonance imaging (BOLD-MRI) comprises a T2-based sequence at 3T, wherein the T2-based sequence at 3T comprises a low rank tensor (LRT).

129. The method of paragraph 124, wherein the cardiovascular system comprises a heart.

130. The method of paragraph 124, wherein the cardiovascular system comprises a myocardium.

131. The method of paragraph 124, wherein the cardiovascular system comprises at least one coronary artery.

132. The method of paragraph 124, wherein the vasodilator is selected from the group consisting of regadenoson, binodenoson, apadenoson, dipyridamole, adenosine, and combinations thereof.

133. The method of paragraph 124, wherein the vasodilator is regadenoson.

134. The method of paragraph 124, wherein the vasodilator induces hyperemia.

135. The method of paragraph 124, wherein the vasodilator is a selective A2A adenosine receptor agonist.

136. The method of paragraph 135, wherein the selective A2A adenosine receptor agonist is regadenoson, or a functional equivalent, analog, derivative or salt.

137. The method of paragraph 124, wherein the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof.

138. The method of paragraph 124, wherein the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

139. The method of paragraph 124, wherein the vasodilator is administered intravascularly, intravenously, intraarterially, or intracoronary.

140. The method of paragraph 124, wherein the vasodilator is administered as a single bolus.

141. The method of paragraph 140, wherein the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

142. The method of paragraph 124, wherein the vasodilator comprises $CO_2$.

143. The method of paragraph 124, wherein the vasodilator is selected from the group consisting of $CO_2$, and an admixture comprising $CO_2$.

144. The method of any one of paragraphs 142 or 143, wherein the vasodilator is administered by inhalation.

145. The method of any one of paragraphs 142 or 143, wherein the vasodilator is administered in a stepwise manner.

146. The method of any one of paragraphs 142 or 143, wherein the vasodilator is administered to the subject so as to reach a predetermined $PaCO_2$ in the subject.

147. The method of paragraph 124, wherein the period of time is selected from a group consisting of at least 1 hour, at least 30 minutes, at least 15 minutes, at least 10 minutes, at least 5 minutes, and at least 1 minute.

148. The method of paragraph 124, wherein the period of time is selected from a group consisting of up to 2 hours, up to 1 hour, up to 30 minutes, up to 15 minutes, and up to 10 minutes.

149. The method of paragraph 124, wherein step (c) is performed about 0.1-0.5, 0.5-1, 1-5, 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b).

150. The method of paragraph 124, wherein no radioactive tracer or contrast agent is administered to the subject.

151. The method of paragraph 124, further comprising comparing the plurality of motion corrected images to assess a response to at least one of oxygenation and blood flow in the cardiovascular system from the subject to a response to at least one of oxygenation and blood flow in the cardiovascular system from a reference sample, wherein a change in the response from the subject relative to the response from the reference sample is indicative of cardiovascular disease in the subject.

152. The method of paragraph 151, wherein the reference sample is obtained from a control subject, wherein the control subject does not have the cardiovascular disease.

153. The method of paragraph 151, wherein the reference sample is obtained from the subject before the subject is treated for the cardiovascular disease.

154. The method of paragraph 151, wherein the reference sample is from a subject that has been successfully treated for the cardiovascular disease.

155. The method of paragraph 124, further comprising comparing the plurality of motion corrected images to assess at least one of vascular reactivity in the cardiovascular system of the subject, wherein a change in the vascular reactivity relative to a reference sample is indicative of cardiovascular disease in the subject.

156. The method of paragraph 155, wherein the change is in an affected territory of the cardiovascular system of the subject.

157. The method of paragraph 155, wherein the change is a decrease in the vascular reactivity relative to a reference sample.

158. The method of paragraph 155, wherein the change is an increase in the vascular reactivity relative to a reference sample.

159. The method of paragraph 155, further comprising calculating and/or measuring and/or determining and/or monitoring and/or detecting and/or assessing at least one selected from the group consisting of a hyperemia response, myocardial perfusion reserve, perfusion, myocardial perfusion, and combinations thereof.

160. The method of paragraph 124, further comprising comparing the plurality of motion corrected images to measure a BOLD signal in the cardiovascular system of the subject, wherein a change in the BOLD signal relative to a reference sample is indicative of cardiovascular disease in the subject.

161. The method of paragraph 160, wherein the change is in an affected territory of the cardiovascular system of the subject.

162. The method of paragraph 160, wherein the change is a decrease in the BOLD signal relative to a reference sample.

163. The method of paragraph 160, wherein the change is an increase in the BOLD signal relative to a reference sample.

164. The method of any one of paragraphs 151, 155, or 160, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease.

165. The method of any one of paragraphs 151, 155, or 160, wherein the cardiovascular disease is ischemic heart disease.

166. The method of any one of paragraphs 151, 155, or 160, wherein the cardiovascular disease is infarcted myocardium.

167. The method of any one of paragraphs 1, 2, 3, 4, 5, 6, 43, 44, 45, 46, 47, 48, 82, 83, 84, 85, 86, 87 or 124, wherein the vasodilator is administered at 0.07 mg/kg/min to 0.28 mg/kg/min.

Some embodiments of the present invention can be defined as any of the following numbered paragraphs:

168. A method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging; wherein the rest images and rest data are obtained at a time interval between each rest image, and wherein the time interval between each rest image is selected from a beat-to-beat heartbeat time interval, a multiple heartbeat time interval, and combinations thereof; administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof, registering the stress images to at least one of the rest images so as to obtain a plurality of motion-corrected images of the at least a portion of the subject's cardiovascular system; comparing the plurality of motion corrected images of the at least a portion of the subject's cardiovascular system to one another so as to determine a response to oxygenation and blood flow in the at least a portion of the subject's cardiovascular system; and comparing the response to oxygenation and blood flow in the at least a portion of the subject's cardiovascular system to a response to oxygenation and blood flow in at least a portion of a cardiovascular system from a reference, wherein a change in the response to oxygenation and blood flow in the at least a portion of the subject's cardiovascular system compared to the response to oxygenation and blood flow in the at least a portion of the cardiovascular system from the reference is a diagnosis of cardiovascular disease in the subject.

169. A method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; and comparing the plurality of motion corrected images of the at least a portion of the subject's cardiovascular system to at least one motion corrected image of at least a portion of a cardiovascular system from a reference, wherein a change in the motion corrected images from the subject compared to the at least one motion corrected image from the reference is a diagnosis of cardiovascular disease in the subject.

170. A method for diagnosing cardiovascular disease in a subject, comprising: imaging at least a portion of the subject's cardiovascular system at rest so as to obtain a series of rest images and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging, wherein the rest images and rest data are obtained at a time interval between each rest image, and wherein the time interval between each rest image is selected from a beat-to-beat heartbeat time interval, a multiple heartbeat time interval, and combinations thereof, administering an effective amount of at least one stress agent to the subject, wherein the stress agent is at least one vasodilator; imaging the at least a portion of the subject's cardiovascular system at stress so as to obtain a series of stress images and stress data of the at least a portion of the subject's cardiovascular system, wherein imaging of the at least a portion of the subject's cardiovascular system at stress comprises operating a magnetic resonance imaging (MRI) scanner and performing blood-contrast-based magnetic resonance imaging, wherein the stress images and stress data are obtained at a time interval between each stress image, and wherein the time interval between each stress image is selected from a beat-to-beat heartbeat time interval, a multiple heartbeat time interval, and combinations thereof; registering the stress images to at least one of the rest images so as to obtain a plurality of motion-corrected images of the at least a portion of the subject's cardiovascular system; comparing the plurality of motion corrected images of the at least a portion of the subject's cardiovascular system to one another to determine vascular reactivity in the at least a portion of the subject's cardiovascular system; and comparing the vascular reactivity in the at least a portion of the subject's cardiovascular system to a vascular reactivity in at least a portion of a cardiovascular system from a reference, wherein a change in the vascular reactivity in the at least a portion of the subject's cardiovascular system compared to the vascular reactivity in the at least a portion of a cardiovascular system from the reference is a diagnosis of cardiovascular disease in the subject.

171. The method of paragraph 168, 169, or 170, wherein the portion of the subject's cardiovascular system is selected from the group consisting of a heart, a portion of a heart, at least one blood vessel, a portion of a blood vessel, and combinations thereof.

172. The method of paragraph 171, wherein the portion of the heart is selected from a myocardium.

173. The method of paragraph 171, wherein the blood vessel is selected from the group consisting of a vein, artery, capillary, and combinations thereof.

174. The method of paragraph 173, wherein the artery is a coronary artery.

175. The method of paragraph 168, 169, or 170, wherein the blood-contrast-based magnetic resonance imaging is selected from the group consisting of perfusion sensitive magnetic resonance imaging, blood oxygenation sensitive magnetic resonance imaging, blood flow sensitive magnetic resonance imaging, blood volume sensitive magnetic resonance imaging, blood-oxygen-level dependent magnetic resonance imaging (BOLD MRI), and combinations thereof.

176. The method of paragraph 168, 169, or 170, wherein the blood-contrast-based magnetic resonance imaging is blood-oxygen-level dependent magnetic resonance imaging (BOLD MRI).

177. The method of paragraph 176, wherein the blood oxygen level dependent magnetic resonance imaging (BOLD-MRI) is not ECG-gated.

178. The method of paragraph 176, wherein the blood oxygen level dependent magnetic resonance imaging (BOLD-MRI) is free-breathing.

179. The method of paragraph 176, wherein the blood oxygen level dependent magnetic resonance imaging (BOLD-MRI) is respiratory and cardiac phase-resolved.

180. The method of paragraph 176, wherein the blood oxygen level dependent magnetic resonance imaging (BOLD-MRI) comprises a T2-based sequence at 3T, wherein the T2-based sequence at 3T comprises a low rank tensor (LRT).

181. The method of paragraph 168, 169, or 170, wherein the vasodilator is selected from the group consisting of regadenoson, binodenoson, apadenoson, dipyridamole, adenosine, and combinations thereof.

182. The method of paragraph 168, 169, or 170, wherein the vasodilator induces hyperemia.

183. The method of paragraph 168, 169, or 170, wherein the vasodilator is a selective A2A adenosine receptor agonist.

184. The method of paragraph 183, wherein the selective A2A adenosine receptor agonist is regadenoson, or a functional equivalent, analog, derivative or salt.

185. The method of paragraph 168, 169, or 170, wherein the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof.

186. The method of paragraph 168, 169, or 170, wherein the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

187. The method of paragraph 168, 169, or 170, wherein the vasodilator is administered intravascularly, intravenously, intraarterially, or intracoronary.

188. The method of paragraph 168, 169, or 170, wherein the vasodilator is administered as a single bolus.

189. The method of paragraph 188, wherein the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

190. The method of paragraph 168, 169, or 170, wherein the vasodilator comprises $CO_2$.

191. The method of paragraph 168, 169, or 170, wherein the vasodilator is selected from the group consisting of $CO_2$, and an admixture comprising $CO_2$.

192. The method of paragraph 190 or 191, wherein the vasodilator is administered by inhalation.

193. The method of paragraph 190 or 191, wherein the vasodilator is administered in a stepwise manner or a block-wise manner.

194. The method of paragraph 190 or 191, wherein the vasodilator is administered to the subject so as to reach a predetermined $PaCO_2$ in the subject.

195. The method of paragraph 168, 169, or 170, wherein the time interval between each rest image is a multiple heartbeat time interval, and wherein the multiple heartbeat time interval is selected from a group consisting of up to 20 minutes, up to 15 minutes, up to 10 minutes, up to 9 minutes, up to 8 minutes, up to 7 minutes, up to 6 minutes, up to 5 minutes, up to 4 minutes, up to 3 minutes, up to 2 minutes, up to 1 minute, up to 45 seconds, up to 30 seconds, up to 15 seconds, up to 10 seconds, and up to 2 seconds.

196. The method of paragraph 168, 169, or 170, wherein the time interval between each stress image is a multiple heartbeat time interval, and wherein the multiple heartbeat time interval is selected from a group consisting of up to 20 minutes, up to 15 minutes, up to 10 minutes, up to 9 minutes, up to 8 minutes, up to 7 minutes, up to 6 minutes, up to 5 minutes, up to 4 minutes, up to 3 minutes, up to 2 minutes, up to 1 minute, up to 45 seconds, up to 30 seconds, up to 15 seconds, up to 10 seconds, and up to 2 seconds.

197. The method of paragraph 168, 169, or 170, wherein no radioactive tracer or contrast agent is administered to the subject.

198. The method of paragraph 168, 169, or 170, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease.

199. The method of paragraph 168, 169, or 170, wherein the reference is a control subject, wherein the control subject does not have the cardiovascular disease.

200. The method of paragraph 168, 169, or 170, wherein the reference is the subject at an earlier point in time.

201. The method of paragraph 168, 169, or 170, wherein the reference is another subject that has been treated for the cardiovascular disease.

202. The method of paragraph 168, 169, or 170, further comprising administering a treatment for cardiovascular disease to the subject 203. The method of paragraph 168, wherein the change in the response to oxygenation and blood flow is a decrease in the response to oxygenation and blood flow in the at least a portion of the subject's cardiovascular system compared to the at least a portion of the cardiovascular system in the reference.

204. The method of paragraph 203, wherein the decrease in the response is in an affected territory of the at least a portion of the subject's cardiovascular system.

205. The method of paragraph 170, wherein the change is an increase in the vascular reactivity in the at least a portion of the subject's cardiovascular system compared to the vascular reactivity in the at least a portion of a cardiovascular system from the reference.

206. The method of paragraph 170, wherein the change is a decrease in the vascular reactivity in the at least a portion of the subject's cardiovascular system compared to the vascular reactivity in the at least a portion of a cardiovascular system from the reference.

207. The method of paragraph 170, further comprising detecting in the subject at least one selected from the group consisting of a hyperemia response, myocardial perfusion reserve, perfusion, myocardial perfusion, and combinations thereof.

208. The method of paragraph 176, wherein the vascular reactivity is indexed as a time constant in a rising part of a BOLD response.

209. The method of paragraph 208, wherein the time constant is a measure of extent of the cardiovascular disease in the subject.

210. The method of paragraph 176, wherein vascular relaxation is indexed as a time constant in a falling part of a BOLD response.

211. The method of paragraph 210, wherein the time constant is a measure of extent of the cardiovascular disease in the subject.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Methods. The proposed cardiac BOLD MRI approach was developed based on a LRT formalism (acquisition and reconstruction) that was previously used for ungated cardiac T1 mapping. It is composed of 3 parts: (i) adiabatic T2 preparation that is repeated at a fixed interval to ensure consistent T2 weighting; (ii) repeat acquisition of a set of central k-space lines with GRE readout every other TR to serve as respiratory and cardiac navigators for reconstruction; and (iii) interleaving of a set of golden-ratio radial GRE readout lines with the navigator lines serving as LRT training data. In brief, we modeled a high-dimensional cardiac image space (cardiac motion (Uc), respiratory motion (Ur), T1 recovery time (Ut), and time after excitation (Ut)) as a low-rank tensor that is partially separable. The complete tensors of all subspaces were recovered from the frequently sampled navigator signal using LRT completion. Subsequently cardiac and respiratory phased-resolved, beat-to-beat cardiac BOLD images were reconstructed. Anesthetized dogs (intact, n=2; and with chronic myocardial infarction, n=2) underwent continuous acquisition in a 3T MRI system (Siemens, Verio) that began 1-minute prior to regadenoson injection (2.5 mg/kg; duration of injection=30 sec) and ended 6 minutes after regadenoson injection. The data acquisition and reconstruction schemes are illustrated in FIG. 1. Sequence parameters were: scan time: 6 mins, delay between T2prep=800 ms; TE (T2prep time)=60 ms; GRE readout (TE/TR=1.4/3.3 ms, flip angle=12°, FOV=270×270 mm2, in-plane resolution: 1.7×1.7 mm2, 1 slice of thickness: 6 mm).

Results. FIG. 2A-FIG. 2F shows a representative time-series of normalized BOLD Response (defined as the BOLD signal normalized by the mean BOLD signal over the first 10 seconds of acquisition) at rest and during regadenoson injection from an intact animal and an animal with chronic MI. LGE images show the region where the BOLD responses were measured. In the healthy myocardium (FIG. 2A, FIG. 2B and FIG. 2C) BOLD Response was relatively stable at rest but, under the influence of regadenoson, it steadily increased over a period of 2-3 minutes and plateaued to more than 10%. In animals with chronic MI (FIG. 2D, FIG. 2E and FIG. 2F), rest BOLD Response was also relatively stable in the infarcted and remote myocardium. However, following regadenoson injection, there was no response in the affected (infarcted) myocardium; but in the remote myocardium, a noticeably delayed hyperemic BOLD Response was observed (compared to intact animals), which peaked ~5 minutes after regadenoson injection and plateaued to above 25%. Similar responses were observed in the other animals as well.

Conclusion. The proposed BOLD approach is the first to enable noninvasive, time-resolved, interrogation of vasomotor differences in vascular beds in health and disease. We envision that this approach has the capacity to open the door for exploring novel insights into coronary circulation in health and disease.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, filed programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefits.

Common forms of computer-readable media may include, for example, a floppy disk, a flexible disk, a hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for imaging a cardiovascular system in a subject, comprising:

imaging at least a portion of the subject's cardiovascular system at rest so as to obtain at least one rest image and rest data of the at least a portion of the subject's cardiovascular system, wherein imaging the at least a portion of the subject's cardiovascular system at rest comprises operating a magnetic resonance imaging (MRI) scanner and performing blood-contrast-based magnetic resonance imaging;

administering at least one stress agent to the subject to induce in the subject a vasodilatory response comprising a rising part corresponding to a rising period followed by a falling part corresponding to a decaying period, wherein the stress agent comprises at least one vasodilator;

imaging the at least a portion of the subject's cardiovascular system at stress at least from beginning of the administration of the at least one stress agent and including the rising period of the vasodilatory response, so as to obtain a series of stress images and stress data of the at least a portion of the subject's cardiovascular system corresponding to at least when the administration begins and the rising part of the vasodilatory response, wherein imaging of the at least a portion of the subject's cardiovascular system at stress comprises operating the magnetic resonance imaging (MRI) scanner and performing the blood-contrast-based magnetic resonance imaging, wherein the stress images and stress data are obtained at a time interval between each stress image, and wherein the time interval between each stress image is a beat-to-beat heartbeat time interval, a multiple heartbeat time interval up to 45 seconds, or combinations thereof;

registering the series of stress images to the at least one rest image so as to obtain a series of motion-corrected images of the at least a portion of the subject's cardiovascular system corresponding to at least when the administration begins and the rising part of the vasodilatory response; and curve fitting the series of the stress data corresponding to from when the administration begins to the rising part of the vasodilatory response as a function of time, and solving therefrom for a time constant of the rising part of the vasodilatory response as an index of vascular reactivity in the rising part of the vasodilatory response of the at least a portion of the subject's cardiovascular system;

wherein the blood-contrast-based magnetic resonance imaging comprises T2 or T2*-based sequences comprising a low rank tensor.

2. The method of claim 1, wherein the portion of the subject's cardiovascular system is selected from the group consisting of a heart, a portion of a heart, at least one blood vessel, a portion of a blood vessel, and combinations thereof, and wherein the portion of the heart comprises a myocardium, the blood vessel comprises a vein, an artery, a capillary, or a combination thereof, and the artery comprises a coronary artery.

3. The method of claim 1, wherein the blood-contrast-based magnetic resonance imaging is selected from the group consisting of perfusion sensitive magnetic resonance imaging, blood oxygenation sensitive magnetic resonance imaging, blood flow sensitive magnetic resonance imaging, blood volume sensitive magnetic resonance imaging, blood-oxygen-level dependent magnetic resonance imaging (BOLD MRI), and combinations thereof.

4. The method of claim 1, wherein the blood-contrast-based magnetic resonance imaging is blood-oxygen-level dependent magnetic resonance imaging (BOLD MRI), wherein the BOLD MRI is characterized by one or more of:
free-breathing,
not ECG-gated, and
respiratory and cardiac phase-resolved.

5. The method of claim 4, wherein the blood oxygen level dependent magnetic resonance imaging (BOLD-MRI) comprises a T2-based sequence, wherein the T2-based sequence comprises the low rank tensor.

6. The method of claim 1, wherein the vasodilator is selected from the group consisting of regadenoson, binodenoson, apadenoson, dipyridamole, adenosine, and combinations thereof.

7. The method of claim 1, wherein the vasodilator is administered at 0.01-10 mg.

8. The method of claim 1, wherein the vasodilator is administered at 0.1-100 µg/kg body weight.

9. The method of claim 1, wherein the vasodilator is administered intravascularly, intravenously, intraarterially, or intracoronary.

10. The method of claim 1, wherein the vasodilator is administered as a single bolus, wherein the single bolus comprises 0.01-10 mg of the vasodilator.

11. The method of claim 1, wherein the vasodilator comprises $CO_2$ and the vasodilator is administered by inhalation in a stepwise or block-wise manner to reach a predetermined $PaCO_2$ in the subject.

12. The method of claim 1, wherein the multiple heartbeat time interval is up to 2 seconds.

13. The method of claim 1, wherein no radioactive tracer or contrast agent is administered to the subject.

14. The method of claim 1, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease.

15. The method of claim 1, further comprising: measuring a difference or an absence thereof in the index of vascular reactivity in the rising part of the vasodilatory response of the at least a portion of the subject's cardiovascular system, compared to that in a reference, wherein the reference is a control subject that does not have the cardiovascular disease, or another subject that has been treated for the cardiovascular disease.

16. The method of claim 1, further comprising: measuring a difference or an absence thereof in the index of vascular reactivity in the rising part of the vasodilatory response of the at least a portion of the subject's cardiovascular system, compared to that in a reference, wherein the reference is a remote territory of the subject not affected by a cardiovascular disease.

17. The method of claim 16, further comprising administering a treatment for cardiovascular disease to the subject measured with a difference in the index of vascular reactivity in the rising part of the vasodilatory response compared to the reference, wherein the treatment comprises coronary revascularization through stenting, coronary bypass grafting, statins, aspirin, or a combination thereof.

18. The method of claim 1, further comprising imaging the at least a portion of the subject's cardiovascular system at stress during the decaying period corresponding to the falling part of the vasodilatory response.

19. The method of claim 1, wherein the multiple heartbeat time interval is up to 10 seconds.

20. The method of claim 1, wherein the multiple heartbeat time interval is up to 15 seconds.

* * * * *